(12) United States Patent
Seroff et al.

(10) Patent No.: US 6,387,403 B1
(45) Date of Patent: May 14, 2002

(54) DOSAGE FORMS AND METHODS FOR PROVIDING EFFECTIVE REBOXETINE THERAPY WITH ONCE-A-DAY DOSING

(75) Inventors: Sylvia L. Seroff; Noymi V. Yam, both of Sunnyvale; Atul D. Ayer, Palo Alto; Padmanabh P. Bhatt, Saratoga; Michael A. Desjardin, Sunnyvale; Andrew C. Lam, South San Francisco; David E. Edgren, Los Altos, all of CA (US); Phillip R. Nixon, Portage, MI (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 09/661,976

(22) Filed: Sep. 14, 2000

Related U.S. Application Data

(60) Provisional application No. 60/153,997, filed on Sep. 15, 1999.

(51) Int. Cl.⁷ .............................. A61K 9/24; A61K 9/20; A61K 9/22
(52) U.S. Cl. ..................... 424/473; 424/464; 424/468; 424/472
(58) Field of Search ................ 424/486, 464, 424/468, 473, 472

(56) References Cited

U.S. PATENT DOCUMENTS

| | | | |
|---|---|---|---|
| 3,845,770 A | 11/1974 | Theeuwes et al. ........... 128/260 |
| 3,916,899 A | 11/1975 | Theeuwes et al. ........... 128/260 |
| 3,995,631 A | 12/1976 | Higuchi et al. ............. 128/260 |
| 4,008,719 A | 2/1977 | Theeuwes et al. ........... 128/260 |
| 4,111,201 A | 9/1978 | Theeuwes .................... 128/260 |
| 4,160,020 A | 7/1979 | Ayer et al. ..................... 424/15 |
| 4,229,449 A | 10/1980 | Melloni et al. ........ 424/248.58 |
| 4,327,725 A | 5/1982 | Cortese et al. .............. 128/260 |
| 4,519,801 A | 5/1985 | Edgren ........................ 604/892 |
| 4,578,075 A | 3/1986 | Urquhart et al. ............ 604/892 |
| 4,681,583 A | 7/1987 | Urquhart et al. ............ 604/892 |
| 5,019,397 A | 5/1991 | Wong et al. ................. 424/473 |
| 5,156,850 A | 10/1992 | Wong et al. ................. 424/473 |
| 5,688,518 A | * 11/1997 | Ayer et al. ................... 424/422 |
| 5,804,209 A | 9/1998 | De Ponti et al. ........... 424/434 |
| 5,935,602 A | * 8/1999 | Dansereau et al. ......... 424/489 |
| 6,028,070 A | 2/2000 | Heiligenstein ........... 514/238.8 |
| 6,046,193 A | 4/2000 | Heiligenstein ........... 514/239.2 |
| 6,066,643 A | 5/2000 | Perry ........................... 514/269 |
| 6,184,222 B1 | * 2/2001 | Heiligenstein ........... 514/239.2 |

FOREIGN PATENT DOCUMENTS

| | | | |
|---|---|---|---|
| GB | 2167407 A | * 11/1984 | |
| GB | 2 167 407 A | 5/1986 | ......... C07D/265/30 |
| WO | WO 99/15176 | 4/1999 | ......... A61K/31/535 |

OTHER PUBLICATIONS

Santus, Giancarlo, Baker, Richard W., "Osmotic Drug Delivery: a review of the patent literature", Journal of Controlled Release, vol. 35 (1995) pp. 1–21, Publisher: Elsevier Science B.V.

Berzewski, H., Van Moffaert, M., and Gagiano, C.A., "Efficacy and tolerability of reboxetine compared with imipramine in a double-bind study in patients suffering from major depressive episodes", European Neuro-Psychopharmacology, vol. 7, Suppl. 1 (1997) pp. 537–547, Publisher, Elsevier Science B.V.

* cited by examiner

Primary Examiner—Thurman K. Page
Assistant Examiner—Rachel M. Bennett
(74) Attorney, Agent, or Firm—Robert R. Neller

(57) ABSTRACT

Dosage forms and methods for providing sustained release of reboxetine are provided. The sustained release dosage forms provide therapeutically effective average steady-state plasma reboxetine concentrations when administered once per day. This once-a-day dosing regimen results in only one peak plasma reboxetine concentration occurrence in each 24 hour period. In addition, the peak plasma reboxetine concentration occurs at a later time following dose administration and exhibits a lesser magnitude than the peak plasma reboxetine concentration that occurs following administration of reboxetine in an immediate-release dosage form.

21 Claims, 6 Drawing Sheets

DOSAGE FORMS AND METHODS FOR PROVIDING EFFECTIVE REBOXETINE THERAPY WITH ONCE-A-DAY DOSING

CROSS-REFERENCE TO RELATED APPLICATIONS

This application claims priority under 35 USC 119(e) of U.S. Ser. No. 60/153,997, filed Sep. 15, 1999, which is incorporated herein by reference.

BACKGROUND OF THE INVENTION

1. Field of the Invention

This invention pertains to dosage forms and methods for providing effective therapy to patients in need of treatment with reboxetine. In particular, the invention is directed to dosage forms and methods for providing sustained release of reboxetine such that once-a-day administration provides effective therapy.

2. Description of the Related Art

All patents and references cited herein are incorporated by reference in their entirety as though fully reproduced herein.

Substituted morpholine derivatives having central nervous system activity and, in particular, antidepressant activity, have been described in U.S. Pat. No. 4,229,449, which is incorporated herein by reference in its entirety. The first compound of this class to be developed as an antidepressant agent is reboxetine having the chemical name 2-[α(2-ethoxyphenoxy)benzyl]morpholine. Reboxetine differs from other available antidepressants by being a selective norepinephrine uptake inhibitor. The evidence suggests that reboxetine is at least as effective as the well-established tricyclic antidepressants and may be as effective as the newer selective serotonin reuptake inhibitors. In addition, reboxetine is well tolerated and appears to have lower potential for adverse drug interactions than some other antidepressants.

U.S. Pat. No. 5,804,209 describes pharmaceutical compositions containing bioadhesive starches and drugs, including, inter alia, reboxetine, primarily for the delivery of drug by the nasal route, although other routes of administration are mentioned. The bioadhesive nature of the starches is described as increasing the time at which the drug remains at the absorption site as compared to drug released from non-bioadhesive compositions. U.S. Pat. Nos. 6,028,070; 6,046,193; and 6,066,643 describe, respectively, a method that uses reboxetine to treat oppositional defiant disorder, a method that uses reboxetine to treat attention-deficit disorder, and pharmaceutical compositions and methods using reboxetine in combination with moxonidine.

Reboxetine methanesulfonate, a pharmaceutically acceptable salt form of the drug, has been available outside of the United States in an immediate-release oral dosage form product of Pharmacia and Upjohn Co. and is currently being evaluated for marketing in the United States. In general, immediate-release dosage forms release essentially the entire dose of drug within a very short period, i.e., minutes, following administration. As this bolus of released drug is absorbed, the plasma drug concentration typically rapidly rises to a maximal or peak concentration and subsequently declines as the drug undergoes "clearance," i.e., becomes distributed, bound or localized within tissues, biotransformed and/or excreted. The rate of drug clearance depends on many factors but will generally be characteristic of a particular drug and may be described by a parameter known as the drug elimination half-life, $t_{1/2}$, defined as the time period during which the plasma drug concentration will decline by one half. Generally, during some portion of the time period in which the plasma drug concentration rises, peaks and subsequently declines, the drug provides its therapeutic effects, i.e., the plasma drug concentration achieves or exceeds a therapeutically effective concentration for the disease or condition being treated. Moreover, at some point during this time period, the therapeutic effects disappear, i.e., when the plasma drug concentration declines to a level that is below a therapeutically effective concentration. In addition, during a portion of this time period surrounding the time the peak concentration is attained, i.e., when the plasma drug concentration is in its highest range, undesired side effects of the drug may often become manifest.

Upon administration of each subsequent dose of the immediate-release dosage form, the plasma drug concentration again rapidly rises to a peak concentration and subsequently declines. When a constant drug dose and dosage form is continuously administered at constant intermittent dosing intervals, a pattern of drug accumulation occurs wherein a "steady-state" of plasma drug concentrations is eventually achieved. The steady-state condition is characterized by a pattern of rising and falling plasma drug concentrations following each administered dose that repeats identically during each dosing interval. The repeating peaks and troughs can be averaged to determine the average steady-state plasma drug concentration that is maintained in the patient. The drug dose, the release rate of the drug dosage form and the length of the dosing interval affect the magnitude of the steady-state plasma concentration peaks and troughs attained in each dosing interval. For drugs administered in immediate-release dosage forms, relatively high peak plasma concentrations following administration generally cannot be avoided. Accordingly, doses and dosing intervals must be selected to obtain an acceptable balance between attaining average steady-state plasma drug concentrations that provide effective therapy and avoiding, as much as possible, problematical peak and/or trough plasma concentrations during each dosing interval.

The effectiveness of antidepressant therapy generally depends on long-term, continuous use of the drug administered at appropriate intervals to maintain a therapeutically effective average steady-state plasma drug concentration during each dosing interval. Antidepressant agents, in general, may be associated with troublesome dose-dependent side effects when peak plasma drug concentrations are relatively high while periods of loss of efficacy may be associated with low trough plasma drug concentrations. Accordingly, manageable dosing intervals suitable for the available dosage strengths for a particular dosage form must be selected to obtain a satisfactory balance between attaining average steady-state plasma drug concentrations that provide effective therapy and avoiding, as much as possible, problematical peak and/or trough plasma concentrations during each dosing interval.

The presently known immediate-release reboxetine dosage form must be administered at least two times per day, i.e., every 12 hours, to provide average steady-state plasma reboxetine concentrations sufficient for therapeutic effectiveness. Drug is rapidly released from the immediate-release dosage form resulting in relatively high peak plasma drug concentrations following each dose. The twice a day administration schedule results in two occurrences of these peak plasma drug concentrations each day. Accordingly, dose-related side effects, such as orthostatic hypotension, that may occur during the time period surrounding the time of these peak plasma drug concentrations may occur twice during each 24 hour period in patients administered conventional reboxetine therapy, i.e., twice-daily doses of immediate release reboxetine.

In view of the above, it would be an advance in the art to provide methods and apparatus for providing patients with effective steady-state plasma reboxetine concentrations while providing relatively lower peak plasma reboxetine concentrations within each dosing interval. In this manner, the potential for peak-associated problems is minimized. In addition, it would be an advance to provide methods and apparatus for providing patients with effective steady-state plasma reboxetine concentrations while providing fewer peak plasma concentrations per day, i.e., by providing an extended dosing interval of, preferably, 24 hours. In this manner, only one peak plasma drug concentration occurs each day thereby also minimizing the potential for any peak-associated problems. Moreover, a once-a-day dosing schedule results in a simpler and more convenient drug therapy regimen that may improve patient compliance, an especially important consideration for long-term therapies such as antidepressant therapy.

Dosage forms for the sustained release of many different pharmaceutical agents are known in the art, however, no such dosage forms or methods for reboxetine are known. While a variety of sustained release dosage forms for delivering certain drugs may be known, not every drug may be suitably delivered from those dosage forms because of various factors including drug solubility, absorption, metabolism and other physical, chemical and physiological parameters that may be unique to the drug and the mode of delivery. Accordingly, a need exists to provide effective dosing methods, dosage forms and devices for once a day dosing of reboxetine.

BRIEF SUMMARY OF THE INVENTION

In one aspect, the invention comprises a sustained release dosage form adapted to release reboxetine, or a pharmaceutically acceptable acid addition salt thereof, at a release rate that results in lower peak plasma reboxetine concentrations following dose administration than are obtained following administration of an immediate-release reboxetine dosage form.

In another aspect, the invention comprises a sustained release dosage form adapted to release reboxetine or a pharmaceutically acceptable acid addition salt thereof, at a release rate such that administration of just one dose per day provides effective reboxetine therapy. In this manner, the number of peak plasma reboxetine concentrations that occur during each 24-hour period is halved compared to the number that occurs with twice-a-day administration of an immediate-release reboxetine dosage form.

Yet another aspect of the present invention comprises methods of administering sustained release reboxetine dosage forms to provide patients with steady-state plasma reboxetine concentrations sufficient to provide effective therapy when administered at dosing intervals of about 24 hours.

A further aspect of the present invention comprises methods of administering sustained release reboxetine dosage forms to provide patients with sufficient steady-state plasma reboxetine concentrations for about 24 hours while providing peak plasma reboxetine concentrations that occur at a later time following dose administration and exhibit a lesser magnitude than the peak plasma reboxetine concentration that occurs following administration of an immediate-release reboxetine dosage form.

Yet another aspect of the present invention comprises a sustained release composition of reboxetine and a carrier. The carrier may be a carbohydrate, including maltodextrin and sugars. The composition may be compressed under forces of about 3500 newtons or greater, typically 3500–5000 newtons.

The above-described features and advantages as well as others will become more apparent from the following detailed disclosure of the invention and the accompanying claims.

BRIEF DESCRIPTION OF THE SEVERAL VIEWS OF THE DRAWINGS

Further objects and advantages of the present invention will become apparent from the following drawings (not drawn to scale) in which.

DETAILED DESCRIPTION OF THE INVENTION

Figure 1:
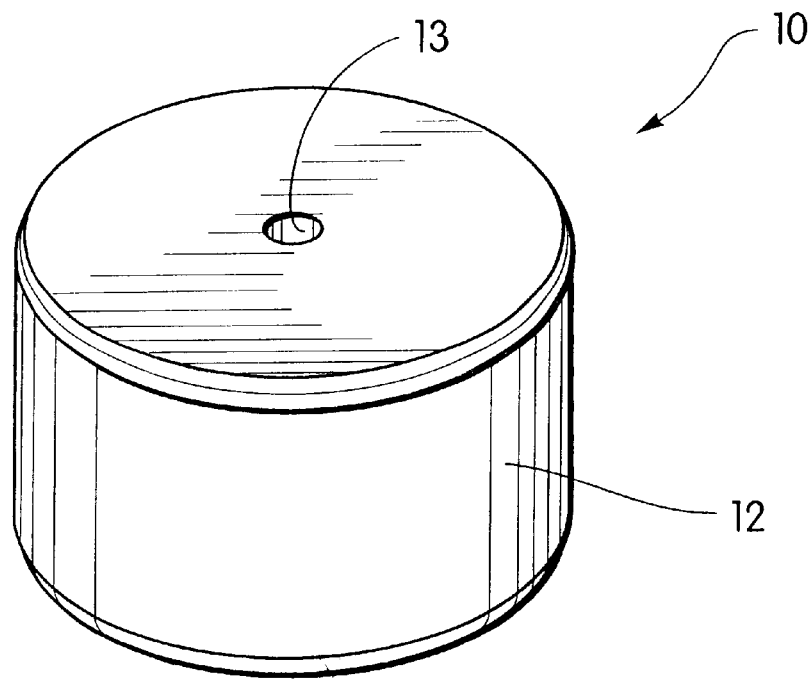
FIG. 1 is a perspective view of an embodiment of a sustained release osmotic dosage form in accord with the present invention.

The present invention is best understood by reference to the following definitions, the drawings and exemplary disclosure provided herein. For purposes of this disclosure, the following definitions shall apply:

The present invention relates to methods and apparatus for providing controlled and sustained delivery of the antidepressant drug, reboxetine. The reboxetine molecule has two asymmetric carbon atoms. Thus, two distinct diastereromers may exist, leading to four distinct enantiomers. The reboxetine drug may be utilized as the racemate (i.e., a non-optically active form of the drug), as a single diastereomer or enantiomer or as mixtures thereof. The free base form of reboxetine, in accord with general pharmaceutical practice, is typically formulated as a pharmaceutically acceptable salt for inclusion in an oral dosage form. Accordingly, the term "reboxetine," unless otherwise indicated, refers to either the free base form or to a pharmaceutically acceptable salt form of the drug, and includes the non-optically-active and optically active forms of the drug,m either individually or as mixtures.

By "pharmaceutically acceptable acid addition salt" or "pharmaceutically acceptable salt", which are used interchangeably herein, are meant those salts in which the anion does not contribute significantly to the toxicity or pharmacological activity of the salt, and, as such, they are the pharmacological equivalent of reboxetine base. These are described in U.S. Pat. No. 4,229,449, which is incorporated in its entirety by reference herein. Examples of pharmaceutically acceptable acids that are useful for the purposes of salt formation include but are not limited to hydrochloric, hydrobromic, hydroiodic, sulfuric, citric, tartaric, methanesulfonic, fumaric, malic, maleic and mandelic, and others.

By "dosage form" is meant a pharmaceutical composition or device comprising an active pharmaceutical agent, such as reboxetine or a pharmaceutically acceptable acid addition salt thereof, the composition or device optionally containing inactive ingredients, i.e., pharmaceutically acceptable excipients such as suspending agents, surfactants, disintegrants, binders, diluents, lubricants, stabilizers, antioxidants, osmotic agents, colorants, plasticizers, coatings and the like, that are used to manufacture and deliver active pharmaceutical agents.

A drug "release rate" refers to the quantity of drug released from a dosage form per unit time, e.g., milligrams of drug released per hour (mg/hr). Drug release rates for drug dosage forms are typically measured as an in vitro rate of dissolution, i.e., a quantity of drug released from the dosage form per unit time measured under appropriate conditions and in a suitable fluid. The dissolution tests utilized in the Examples described herein were performed on dosage forms placed in metal coil sample holders attached to a USP Type VII bath indexer and immersed in about 50 ml of acidified water (pH=3) equilibrated in a constant temperature water bath at 37° C. Aliquots of the release rate solutions were injected into a chromatographic system to quantify the amounts of drug released during the testing intervals.

For clarity and convenience herein, the convention is utilized of designating the time of drug administration as zero hours (t=0 hours) and times following administration in appropriate time units, e.g., t=30 minutes or t=2 hours, etc.

As used herein, unless otherwise specified, a drug release rate obtained at a specified time "following administration" refers to the in vitro drug release rate obtained at the specified time following implementation of an appropriate dissolution test. The time at which a specified percentage of the drug within a dosage form has been released may be referenced as the "$T_x$" value, where "x" is the percent of drug that has been released. For example, a commonly used reference measurement for evaluating drug release from dosage forms is the time at which 90% of drug within the dosage form has been released. This measurement is referred to as the "$T_{90}$" for the dosage form.

An "immediate-release dosage form" refers to a dosage form that releases drug substantially completely within a short time period following administration, i.e., generally within a few minutes to about 1 hour.

By "sustained release dosage form" is meant a dosage form that releases drug substantially continuously for many hours. Sustained release dosage forms in accord with the present invention exhibit $T_{90}$ values of at least about 8 hours or more and preferably about 15 hours or more. The dosage forms continuously release drug for sustained periods of at least about 10 hours, preferably 12 hours or more and, more preferably, 16–20 hours or more.

Dosage forms in accord with the present invention exhibit uniform release rates of reboxetine for a prolonged period of time within the sustained release time period. By "uniform release rate" is meant an average hourly release rate that varies by no more than about 30% and preferably no more than about 25% from either the preceding or the subsequent average hourly release rate. By "prolonged period of time" is meant a continuous period of time of at least about 4 hours, preferably 6–8 hours or more and, more preferably, 10 hours or more. For example, the exemplary osmotic dosage forms described herein generally begin releasing reboxetine at a uniform release rate within about 2 to about 6 hours following administration and the uniform rate of release continues for a prolonged period of time, as defined above, until at least about 75% and preferably at least about 85% of the drug is released from the dosage form. Release of reboxetine continues thereafter for several more hours although the rate of release is generally slowed somewhat from the uniform release rate.

One commonly-used indicator of drug availability is the concentration of drug that is obtained within the blood or plasma, or other appropriate body fluid or tissue, of a patient following administration of the drug, generally expressed as mass per unit volume, typically nanograms per milliliter. For convenience, this concentration ("$C_p$") may be referred to as "plasma drug concentration" or "plasma concentration" herein which is intended to be inclusive of drug concentration measured in any appropriate body fluid or tissue. The plasma drug concentration at any time following drug administration is referenced as $C_{time}$, as in $C_{9h}$ or $C_{24h}$, etc.

A pattern of drug accumulation following continuous administration of a constant dose and dosage form at constant dosing intervals eventually achieves a "steady-state" where the plasma concentration peaks and plasma concentration troughs are essentially identical within each dosing interval. As used herein, the steady-state maximal (peak) plasma drug concentration is referenced as $C_{max}$ and the minimal (trough) plasma drug concentration is referenced as $C_{min}$. The time following drug administration at which the steady-state peak plasma and trough drug concentrations occur are referenced as the $T_{max}$ and the $T_{min}$, respectively.

Persons of skill in the art appreciate that plasma drug concentrations obtained in individual subjects will vary due to intrapatient variability in the many parameters affecting drug absorption, distribution, metabolism and excretion. For this reason, unless otherwise indicated, mean values obtained from groups of subjects are used herein for purposes of comparing plasma drug concentration data and for analyzing relationships between in vitro dosage form dissolution rates and in vivo plasma drug concentrations.

A relationship between an administered dose of reboxetine and the magnitude of the peak plasma reboxetine concentration obtained following dose administration is used herein to illustrate significant differences between the dosage forms and methods of the present invention and prior art dosage forms. For example, as described below in more detail, a unitless numerical value is derived by calculating the ratio of the numerical value of the mean $C_{max}$ (ng/ml) to the numerical value of the dose (mg), i.e., $C_{max}$/dose. The difference in the values of the derived ratios characterize the reduction in the magnitude of peak plasma reboxetine concentrations following administration of the sustained release reboxetine dosage forms of the present invention compared to peak plasma reboxetine concentrations following administration of conventional immediate-release reboxetine dosage forms. Administration of dosage forms in accord with the present invention preferably provides steady-state $C_{max}$/dose ratios of less than about 30 and more preferably less than about 25.

It has been surprisingly discovered that sustained release reboxetine dosage forms exhibiting $T_{90}$ values of 8 hours or more and more preferably 15 hours or more and which release reboxetine at a uniform release rate for a prolonged period of time can be prepared. Administration of such dosage forms once daily provides therapeutically effective average steady-state plasma reboxetine concentrations. The exemplary sustained release reboxetine dosage forms, methods of preparing such dosage forms and methods of using such dosage forms described herein are directed to osmotic dosage forms for oral administration. In addition to osmotic systems as described herein, however, there are many other approaches to achieving sustained release of drugs from oral dosage forms known in the art. These different approaches include, for example, diffusion systems such as reservoir devices and matrix devices, dissolution systems such as encapsulated dissolution systems (including, for example, "tiny time pills") and matrix dissolution systems, combination diffusion/dissolution systems and ion-exchange resin systems as described in *Remington's Pharmaceutical Sciences*, 1990 ed., pp. 1682–1685. Reboxetine dosage forms that operate in accord with these other approaches are encompassed by the scope of the claims below to the extent that the drug release characteristics and/or the plasma reboxetine concentration characteristics as recited in the claims describe those dosage forms either literally or equivalently.

Osmotic dosage forms, in general, utilize osmotic pressure to generate a driving force for imbibing fluid into a compartment formed, at least in part, by a semipermeable wall that permits free diffusion of fluid but not drug or osmotic agent(s), if present. A significant advantage to osmotic systems is that operation is pH-independent and thus continues at the osmotically determined rate throughout an extended time period even as the dosage form transits the gastrointestinal tract and encounters differing microenvironments having significantly different pH values. A review of such dosage forms is found in Santus and Baker, "Osmotic drug delivery: a review of the patent literature," *Journal of Controlled Release* 35 (1995) 1–21, incorporated in its entirety by reference herein. In particular, the following U.S. Patents, owned by the assignee of the present application, ALZA Corporation, directed to osmotic dosage forms, are each incorporated in their entirety herein: U.S. Pat. Nos. 3,845,770; 3,916,899; 3,995,631; 4,008,719; 4,111,202; 4,160,020; 4,327,725; 4,519,801; 4,578,075; 4,681,583; 5,019,397; and 5,156,850.

FIG. 1 is a perspective view of one embodiment of a sustained release osmotic dosage form in accord with the present invention. The dosage form 10 comprises a wall 12 that surrounds and encloses an internal compartment (not seen in FIG. 1). The internal compartment contains a composition comprising reboxetine, or a pharmaceutically acceptable acid addition salt thereof, as described in more detail below. Wall 12 is provided with at least one drug delivery orifice 13 for connecting the internal compartment with the exterior environment of use. Accordingly, following oral ingestion of the dosage form 10, fluid is imbibed through wall 12 and reboxetine is released through delivery orifice 13.

In certain embodiments of the present invention, the internal compartment contains a single component layer referred to herein as a drug layer, comprising reboxetine in an admixture with selected excipients adapted to provide an osmotic activity gradient for driving fluid from an external environment through wall 12 and for forming a deliverable reboxetine formulation upon imbibition of this fluid. As described in more detail below, the excipients may include a suitable suspending agent, also referred to herein as a drug carrier, and an osmotically active agent, i.e., an "osmagent." Other excipients such as lubricants, binders, etc. may also be included. In operation, following oral ingestion of the dosage form 10, the osmotic activity gradient across wall 12 causes gastric fluid to be imbibed through the wall 12 thereby forming a deliverable reboxetine formulation, i.e., a solution or suspension, within the internal compartment. The deliverable reboxetine formulation is released through delivery orifice 13 as fluid continues to enter the internal compartment. As release of drug formulation occurs, fluid continues to be imbibed thereby driving continued release. In this manner, reboxetine is released in a sustained and continuous manner over an extended time period.

Figure 2:
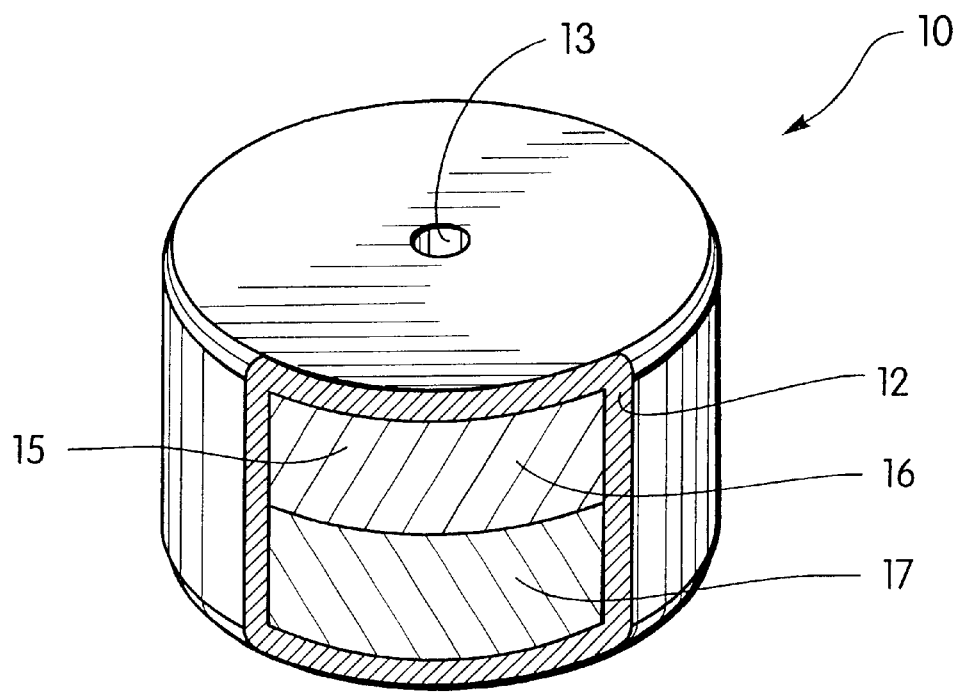
FIG. 2 is a cutaway view of another embodiment of a dosage form in accord with the present invention illustrating a bilayered dosage form.

FIG. 2 is a cutaway view of another embodiment of a dosage form in accord with the present invention. In this embodiment, internal compartment 15 contains a bilayered compressed core having a first component drug layer 16 and a second component push layer 17. Drug layer 16, as described above with reference to FIG. 1, comprises reboxetine in an admixture with selected excipients. As described in more detail below, the second component push layer 17 comprises osmotically active component(s) but does not contain drug. The osmotically active component(s) in the second component layer typically comprise an osmagent and one or more osmopolymer(s) having relatively large molecular weights which exhibit swelling as fluid is imbibed such that release of these osmopolymers through the drug delivery orifice 13 does not occur. Additional excipients such as binders, lubricants, antioxidants and colorants may also be included in push layer 17. The second component layer is referred to herein as an expandable or a push layer since, as fluid is imbibed, the osmopolymer(s) swell and push against the deliverable drug formulation of the first component drug layer to thereby facilitate release of the drug formulation from the dosage form. In operation, following oral ingestion of the dosage form 10, the osmotic activity gradient across wall 12 causes gastric fluid to be imbibed through the wall 12 thereby forming the first component drug layer 16 into a deliverable reboxetine formulation and concurrently swelling the osmopolymer(s) in the second component push layer 17. The deliverable reboxetine formulation is released through delivery orifice 13 as fluid continues to enter the internal compartment and the push layer continues to swell. As release of drug formulation occurs, fluid continues to be imbibed and the push layer continues to swell thereby driving continued release. In this manner, reboxetine is released in a sustained and continuous manner over an extended time period.

Figure 3:
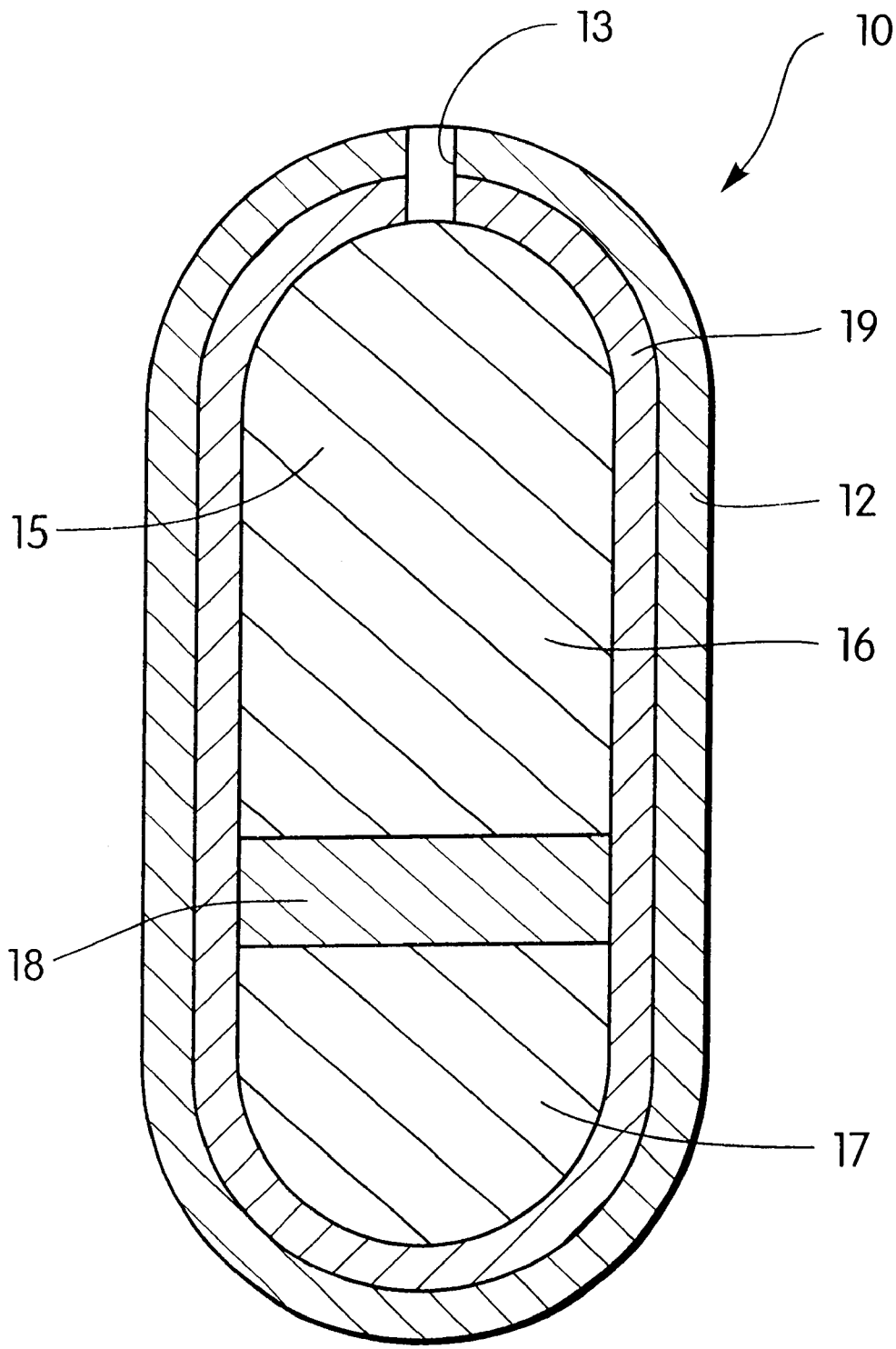
FIG. 3 is a cross-sectional view of yet another embodiment of a dosage form in accord with the present invention illustrating a trilayered dosage form.

FIG. 3 is a cross-sectional view of yet another embodiment of a dosage form in accord with the present invention. In this embodiment, the internal compartment 15 contains a trilayered compressed core having a first component drug layer 16, a second component push layer 17, and a third component barrier layer 18 separating drug layer 16 from push layer 17. The embodiment of the dosage form 10 illustrated in FIG. 3 also includes an inner wall 19, an outer wall 12 and a delivery orifice 13. Drug layer 16, as described with reference to FIG. 1, comprises reboxetine in an admixture with selected excipients. Push layer 17, as described with reference to FIG. 2, comprises osmotically active component(s) but does not contain drug. The composition of third component barrier layer 18 is inert with the respect to the composition of the drug layer 16 and substantially impermeable, such that drug from drug layer 16 and the components of the composition of push layer 17 are prevented from mixing. Inner wall 19 is permeable to the passage of gastric fluid entering compartment 15 and provides a lubricating function that facilitates the movement of drug layer 16, push layer 17 and barrier layer 18 toward delivery orifice 13. Inner wall 19 may be formed from hydrophilic materials and excipients. Outer wall 12 is semipermeable, allowing gastric fluid to enter compartment 15 but preventing the passage of the materials comprising the core in compartment 15. The deliverable reboxetine formulation is released from delivery orifice 13 as described above with respect to the embodiment of FIG. 2.

Wall 12 is formed to be permeable to the passage of an external fluid, such as water and biological fluids, and it is substantially impermeable to the passage of reboxetine, osmagent, osmopolymer and the like. As such, it is semipermeable. The selectively semipermeable compositions used for forming the wall are essentially nonerodible and they are insoluble in biological fluids during the life of the dosage form.

Representative polymers for forming wall 12 comprise semipermeable homopolymers, semipermeable copolymers, and the like. Such materials comprise cellulose esters, cellulose ethers and cellulose ester-ethers. The cellulosic polymers have a degree of substitution (DS) of their anhydroglucose unit of from greater than 0 up to 3, inclusive. Degree of substitution (DS) means the average number of hydroxyl groups originally present on the anhydroglucose unit that are replaced by a substituting group or converted into another group. The anhydroglucose unit can be partially or completely substituted with groups such as acyl, alkanoyl, alkenoyl, aroyl, alkyl, alkoxy, halogen, carboalkyl, alkylcarbamate, alkylcarbonate, alkylsulfonate, alkysulfamate, semipermeable polymer forming groups, and the like, wherein the organic moieties contain from one to twelve carbon atoms, and preferably from one to eight carbon atoms.

The semipermeable compositions typically include a member selected from the group consisting of cellulose acylate, cellulose diacylate, cellulose triacylate, cellulose acetate, cellulose diacetate, cellulose triacetate, mono-, di- and tri-cellulose alkanylates, mono-, di-, and tri-alkenylates, mono-, di-, and tri-aroylates, and the like. Exemplary polymers include cellulose acetate having a DS of 1.8 to 2.3 and an acetyl content of 32 to 39.9%; cellulose diacetate having a DS of 1 to 2 and an acetyl content of 21 to 35%; cellulose triacetate having a DS of 2 to 3 and an acetyl content of 34 to 44.8%; and the like. More specific cellulosic polymers include cellulose propionate having a DS of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45%, and a hydroxyl content of 2.8 to 5.4%; cellulose acetate butyrate having a DS of 1.8, an acetyl content of 13 to 15%, and a butyryl content of 34 to 39%; cellulose acetate butyrate having an acetyl content of 2 to 29%, a butyryl content of 17 to 53%, and a hydroxyl content of 0.5 to 4.7%; cellulose triacylates having a DS of 2.6 to 3, such as cellulose trivalerate, cellulose trilamate, cellulose tripalmitate, cellulose trioctanoate and cellulose tripropionate; cellulose diesters having a DS of 2.2 to 2.6, such as cellulose disuccinate, cellulose dipalmitate, cellulose dioctanoate, cellulose dicaprylate, and the like; and mixed cellulose esters, such as cellulose acetate valerate, cellulose acetate succinate, cellulose propionate succinate, cellulose acetate octanoate, cellulose valerate palmitate, cellulose acetate heptanoate, and the like. Semipermeable polymers are known in U.S. Pat. No. 4,077,407, and they can be synthesized by procedures described in *Encyclopedia of Polymer Science and Technology*, Vol. 3, pp. 325–354 (1964), Interscience Publishers Inc., New York, N.Y.

Additional semipermeable polymers for forming the outer wall 12 comprise cellulose acetaldehyde dimethyl acetate; cellulose acetate ethylcarbamate; cellulose acetate methyl carbamate; cellulose dimethylaminoacetate; semipermeable polyamide; semipermeable polyurethanes; semipermeable sulfonated polystyrenes; cross-linked selectively semipermeable polymers formed by the coprecipitation of an anion and a cation, as disclosed in U.S. Pat. Nos. 3,173,876; 3,276,586; 3,541,005; 3,541,006 and 3,546,142; semipermeable polymers, as disclosed by Loeb, et al. in U.S. Pat. No. 3,133,132; semipermeable polystyrene derivatives; semipermeable poly(sodium styrenesulfonate); semipermeable poly(vinylbenzyltrimethylammonium chloride); and semipermeable polymers exhibiting a fluid permeability of $10^{-5}$ to $10^{-2}$ (cc. mil/cm hr.atm), expressed as per atmosphere of hydrostatic or osmotic pressure differences across a semipermeable wall. The polymers are known to the art in U.S. Pat. Nos. 3,845,770; 3,916,899 and 4,160,020; and in Handbook of Common Polymers, Scott and Roff (1971) CRC Press, Cleveland, Ohio.

Wall 12 may also comprise a flux-regulating agent. The flux regulating agent is a compound added to assist in regulating the fluid permeability or flux through wall 12. The flux-regulating agent can be a flux-enhancing agent or a flux-decreasing agent. The agent can be preselected to increase or decrease the liquid flux. Agents that produce a marked increase in permeability to fluid such as water are often essentially hydrophilic, while those that produce a marked decrease to fluids such as water are essentially hydrophobic. The amount of regulator in the wall when incorporated therein generally is from about 0.01% to 20% by weight or more. The flux regulator agents may include polyhydric alcohols, polyalkylene glycols, polyalkylenediols, polyesters of alkylene glycols, and the like. Typical flux enhancers include polyethylene glycol 300, 400, 600, 1500, 4000, 6000 and the like; low molecular weight glycols such as polypropylene glycol, polybutylene glycol and polyamylene glycol: the polyalkylenediols such as poly(1,3-propanediol), poly(1,4-butanediol), poly(1,6-hexanediol), and the like; aliphatic diols such as 1,3-butylene glycol, 1,4-pentamethylene glycol, 1,4-hexamethylene glycol, and the like; alkylene triols such as glycerine, 1,2,3-butanetriol, 1,2,4-hexanetriol, 1,3,6-hexanetriol and the like; esters such as ethylene glycol dipropionate, ethylene glycol butyrate, butylene glycol dipropionate, glycerol acetate esters, and the like. Presently preferred flux enhancers include the group of difunctional block-copolymer polyoxyalkylene derivatives of propylene glycol known as pluronics (BASF). Representative flux-decreasing agents include phthalates substituted with an alkyl or alkoxy or with both an alkyl and alkoxy group such as diethyl phthalate, dimethoxyethyl phthalate, dimethyl phthalate, and [di(2-ethylhexyl) phthalate], aryl phthalates such as triphenyl phthalate, and butyl benzyl phthalate; insoluble salts such as calcium sulfate, barium sulfate, calcium phosphate, and the like; insoluble oxides such as titanium oxide; polymers in powder, granule and like form such as polystyrene, polymethylmethacrylate, polycarbonate, and polysulfone; esters such as citric acid esters esterified with long chain alkyl groups; inert and substantially water impermeable fillers; resins compatible with cellulose based wall forming materials, and the like.

Other materials that may be included in the semipermeable wall material for imparting flexibility and elongation properties to the wall, for making wall 12 less-to-nonbrittle and to render tear strength. Suitable materials include phthalate plasticizers such as dibenzyl phthalate, dihexyl phthalate, butyl octyl phthalate, straight chain phthalates of six to eleven carbons, di-isononyl phthalte, di-isodecyl phthalate, and the like. The plasticizers include nonphthalates such as triacetin, dioctyl azelate, epoxidized tallate, tri-isoctyl trimellitate, tri-isononyl trimellitate, sucrose acetate isobutyrate, epoxidized soybean oil, and the like. The amount of plasticizer in a wall when incorporated therein is about 0.01 % to 20% weight, or higher.

The second component expandable, i.e., push, layer 17 comprises a push-displacement composition in contacting layered arrangement with the first component drug layer 16 as illustrated in FIG. 2 or in contacting layered arrangement with barrier layer 18 as illustrated in FIG. 3. The push layer comprises a polymer that imbibes an aqueous or biological fluid and swells to push the drug composition through the exit means of the device. A polymer having suitable imbibition properties may be referred to herein as an osmopolymer. The osmopolymers are swellable, hydrophilic polymers that interact with water and aqueous biological fluids and swell or expand to a high degree, typically exhibiting a 2–50 fold volume increase. The osmopolymer can be non-crosslinked or crosslinked, but in a preferred embodiment are at least lightly crosslinked to create a polymer network that is too large and entangled to exit the dosage form. Thus, in a preferred embodiment, the expandable composition is retained within the dosage form during its operative lifetime.

Representatives of fluid-imbibing displacement polymers comprise members selected from poly(alkylene oxide) of 1 million to 15 million number-average molecular weight, as represented by poly(ethylene oxide), and poly(alkali carboxymethylcellulose) of 500,000 to 3,500,000 number-average molecular weight, wherein the alkali is sodium, potassium or lithium. Examples of additional polymers for the formulation of the push-displacement composition comprise osmopolymers comprising polymers that form hydrogels, such as Carbopol® acidic carboxypolymer, a polymer of acrylic cross-linked with a polyallyl sucrose, also known as carboxypolymethylene, and carboxyvinyl polymer having a molecular weight of 250,000 to 4,000,000; Cyanamer® polyacrylamides; cross-linked water swellable indenemaleic anhydride polymers; Good-rite® polyacrylic acid having a molecular weight of 80,000 to 200,000; Aqua-Keeps® acrylate polymer polysaccharides composed of condensed glucose units, such as diester cross-linked polygluran; and the like. Representative polymers that form hydrogels are known to the prior art in U.S. Pat. No. 3,865,108, issued to Hartop; U.S. Pat. No. 4,002,173, issued to Manning; U.S. Pat. No. 4,207,893, issued to Michaels; and in *Handbook of Common Polymers*, Scott and Roff, Chemical Rubber Co., Cleveland, Ohio.

Suitable osmagents, also known as osmotic solutes and osmotically effective agents, that may be found in both the drug layer and the push layer, if included, in the dosage form are those which exhibit an osmotic activity gradient across the wall 12. Suitable osmagents comprise a member selected from the group consisting of sodium chloride, potassium chloride, lithium chloride, magnesium sulfate, magnesium chloride, potassium sulfate, sodium sulfate, lithium sulfate, potassium acid phosphate, mannitol, urea, inositol, magnesium succinate, tartaric acid, raffinose, sucrose, glucose, lactose, sorbitol, inorganic salts, organic salts and carbohydrates.

Exemplary solvents suitable for manufacturing the dosage form components comprise aqueous or inert organic solvents that do not adversely harm the materials used in the system. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride nitroethane, nitropropane tetrachloroethane, ethyl ether, isopropyl ether, cyclohexane, cyclooctane, benzene, toluene, naphtha, 1,4-dioxane, tetrahydrofuran, diglyme, water, aqueous solvents containing inorganic salts such as sodium chloride, calcium chloride, and the like, and mixtures thereof such as acetone and water, acetone and methanol, acetone and ethyl alcohol, methylene dichloride and methanol, and ethylene dichloride and methanol.

Barrier layer 18 comprises a material that is inert with respect to the composition of drug layer 16 and impermeable so as to prevent the drug in drug layer 16 from migrating into push layer 17. Suitable materials include water-insoluble polymers, fats, fafty acids and fatty acid esters that are solids at ambient and body temperatures, and waxes. Representative water-insoluble polymers include ethyl cellulose, cellulose acetate, polyvinylchloride, copolymers of polyethylene and vinyl acetate, poly(methylmethacrylate), acrylic polymers such as Eudragite®L or Eudragit®R, polycaprolactone, poly(lactic-co-glycolic) acid polymers (PLGA), high density polyethylene, rubber, styrene butadiene, polysilicone, nylon, , polystyrene, polytetrafluoroethylene, and halogenated polymers. Representative waxes include paraffin wax and beeswax. Representative fats, fatty acids and fatty acid esters include $C_{16}$–$C_{24}$ long chain fatty acids, esters of such long chain fatty acids such as stearic acid and oleic acid, and mixtures of the foregoing. Mixtures of the above-described materials may be utilized, e.g., a mixture of ethyl cellulose and stearic acid, which is presently preferred.

Inner wall 19 comprises a member selected from hydrogels, gelatin, low molecular weight polyethylene oxides, e.g., less than 100,000 MW, hydroxyalkylcellu loses, e.g., hydroxyethylcellulose, hydroxypropylcellulose, hydroxyisopropylcelluose, hydroxybutylcellulose and hydroxyphenylcellulose, and hydroxyalkyl alkylcelluloses, e.g., hydroxypropyl methylcellulose, and mixtures thereof. The hydroxyalkylcelluloses comprises polymers having a 9,500 to 1,250,000 number-average molecular weight. For example, hydroxypropyl celluloses having number average molecular weights of between 80,000 to 850,000 are useful. Inner wall 19 may be prepared from conventional solutions or suspensions of the aforementioned materials in aqueous solvents or inert organic solvents. Preferred materials for inner wall 19 include hydroxypropyl cellulose, hydroxyethyl cellulose, hydroxypropyl methyl cellulose, povidone [poly (vinylpyrrolidone)], polyethylene glycol, and mixtures thereof. More preferred are mixtures of hydroxypropyl cellulose and povidone, prepared in organic solvents, particularly organic polar solvents such as lower alkanols having 1–8 carbon atoms, preferably ethanol, mixtures of hydroxyethyl cellulose and hydroxypropyl methyl cellulose prepared in aqueous solution, and mixtures of hydroxyethyl cellulose and polyethylene glycol prepared in aqueous solution. Most preferably, inner wall 19 comprises a mixture of hydroxypropyl cellulose and povidone prepared in ethanol. Conveniently, inner wall 19 may be applied as a subcoat by conventional coating procedures. The weight of the subcoat applied to the trilayered core may be correlated with the thickness of the subcoat. During manufacturing operations, the thickness of the subcoat may be controlled by controlling the weight of the subcoat taken up in a coating operation.

The drug layer 16 comprises a composition formed of a pharmaceutically effective amount of reboxetine, or a pharmaceutically acceptable salt thereof, and a carrier. The carrier may comprise a hydrophilic polymer. The hydrophilic polymer provides a hydrophilic polymer particle in the drug composition that contributes to the uniform release rate of active agent and controlled delivery pattern. Representative examples of these polymers are poly(alkylene oxide) of 100,000 to 750,000 number-average molecular weight, including poly(ethylene oxide), poly(methylene oxide), poly(butylene oxide) and poly(hexylene oxide); and a poly(carboxymethylcellulose) of 40,000 to 400,000 number-average molecular weight, represented by poly (alkali carboxymethylcellulose), poly(sodium carboxymethylcellulose), poly(potassium carboxymethylcellulose) and poly(lithium carboxymethylcellulose). The drug composition can comprise a hydroxypropylalkylcellulose of 9,200 to 125,000 number-average molecular weight for enhancing the delivery properties of the dosage form as represented by hydroxypropylethylcellulose, hydroxypropylmethylcellulose, hydroxypropylbutylcellulose and hydroxypropylpentylcellulose; and a poly (vinylpyrrolidone) of 7,000 to 75,000 number-average molecular weight for enhancing the flow properties of the dosage form. Preferred among those polymers are the poly (ethylene oxide) of 100,000–300,000 number average molecular weight. Carriers that erode in the gastric environment, i.e., bioerodible carriers, are especially preferred.

Other carriers that may be incorporated into drug layer 17 include carbohydrates that exhibit sufficient osmotic activity to be used alone or with other osmagents. Such carbohydrates comprise monsaccharides, disaccharides and polysaccharides. Representative examples include maltodextrins (i.e., glucose polymers produced by the hydrolysis of corn starch) and the sugars comprising lactose, glucose, raffinose, sucrose, mannitol, sorbitol, and the like. Preferred maltodextrins are those having a dextrose equivalence (DE) of 20 or less, preferably with a DE ranging from about 4 to about 20, and often 9–20. Maltodextrin having a DE of 9–12 has been found to be useful.

It has been discovered that the carbohydrates described above, preferably the maltodextrins, may be used in the drug layer 17 without the addition of another osmagent, and obtain the desired release of reboxetine from the dosage form, while providing a therapeutic effect over a prolonged period of time and up to 24 hours with once-a-day dosing. An additional benefit of the use of those materials as the carrier is that they exhibit minimal reactivity with the reboxetine molecule, which contains a relatively reactive secondary amine moiety that may react with excipients and impurities to form degradation products. Consequently, compositions of reboxetine and the above-described carbohydrates, especially maltodextrin, are stable (i.e., form minimal amounts of degradation products over time) over longer periods of time than if other excipients are used. Long term stability of the compositions allows for preparation of dosage forms that exhibit long shelf life, adding to the economic benefits of the once-a-day dosage forms described herein.

The reboxetine layer typically will be a dry composition formed by compression of the carrier and the drug as one layer and the expandable or push layer, when included, as a second contacting layer. The drug layer 16 is formed as a mixture containing reboxetine and the drug carrier. The drug layer may be formed from particles by comminution that produces the size of the drug and the size of the accompanying polymer used in the fabrication of the drug layer, typically as a core containing the compound, according to the mode and the manner of the invention. The means for producing particles include granulation, spray drying, sieving, lyophilization, crushing, grinding, jet milling, micronizing and chopping to produce the intended micron particle size. The process can be performed by size reduction equipment, such as a micropulverizer mill, a fluid energy grinding mill, a grinding mill, a roller mill, a hammer mill, an attrition mill, a chaser mill, a ball mill, a vibrating ball mill, an impact pulverizer mill, a centrifugal pulverizer, a coarse crusher and a fine crusher. The size of the particle can be ascertained by screening, including a grizzly screen, a flat screen, a vibrating screen, a revolving screen, a shaking screen, an oscillating screen and a reciprocating screen. The processes and equipment for preparing drug and carrier particles are disclosed in *Pharmaceutical Sciences*, Remington, 17th Ed., pp. 1585–1594 (1985); *Chemical Engineers Handbook*, Perry, 6th Ed., pp. 21–13 to 21–19 (1984); *Journal of Pharmaceutical Sciences*, Parrot, Vol. 61, No. 6, pp. 813–829 (1974); and *Chemical Engineer*, Hixon, pp. 94–103 (1990).

Optionally, surfactants and disintegrants may be utilized in the drug layer. Exemplary of the surfactants are those having an HLB value of between about 10–25, such as polyethylene glycol 400 monostearate, polyoxyethylene-4-sorbitan monolaurate, polyoxyethylene-20-sorbitan monooleate, polyoxyethylene-20-sorbitan monopalmitate, polyoxyethylene-20-monolaurate, polyoxyethylene-40-stearate, sodium oleate and the like. Disintegrants may be selected from starches, clays, celluloses, algins and gums and crosslinked starches, celluloses and polymers. Representative disintegrants include corn starch, potato starch, croscarmelose, crospovidone, sodium starch glycolate, Veegum HV, methylcellulose, agar, bentonite, carboxymethylcellulose, alginic acid, guar gum and the like.

Pan coating may be conveniently used to provide the completed dosage form, except for the exit orifice. In the pan coating system, the wall-forming composition for the inner wall or the semipermeable wall, as the case may be, is deposited by successive spraying of the appropriate wall composition onto the compressed single, bilayered or trilayered core comprising the drug layer for the single layer core; the drug layer and the push layer for the bilayered core; or the drug layer, barrier layer and push layer for the trilayered core, accompanied by tumbling in a rotating pan. A pan coater is used because of its availability at commercial scale. Other techniques can be used for coating the compressed core. Once coated, the wall is dried in a forced-air oven or in a temperature and humidity controlled oven to free the dosage form of solvent(s) used in the manufacturing. Drying conditions will be conventionally chosen on the basis of available equipment, ambient conditions, solvents, coatings, coating thickness, and the like.

Other coating techniques can also be employed. For example, the wall or walls of the dosage form may be formed in one technique using the air-suspension procedure. This procedure consists of suspending and tumbling the compressed single, bilayer or trilayer core in a current of air and the semipermeable wall forming composition, until the wall is applied to the core. The air-suspension procedure is well suited for independently forming the wall of the dosage form. The air-suspension procedure is described in U.S. Pat. No. 2,799,241; in *J. Am. Pharm. Assoc.*, Vol. 48, pp.

451–459 (1959); and, ibid., Vol. 49, pp. 82–84 (1960). The dosage form also can be coated with a Wurster® air-suspension coater using, for example, methylene dichloride methanol as a cosolvent for the wall forming material. An Aeromatice® air-suspension coater can be used employing a cosolvent.

Dosage forms in accord with the present invention are manufactured by standard techniques. For example, the dosage form may be manufactured by the wet granulation technique. In the wet granulation technique, the drug and carrier are blended using an organic solvent, such as denatured anhydrous ethanol, as the granulation fluid. The remaining ingredients can be dissolved in a portion of the granulation fluid, such as the solvent described above, and this latter prepared wet blend is slowly added to the drug blend with continual mixing in the blender. The granulating fluid is added until a wet blend is produced, which wet mass blend is then forced through a predetermined screen onto oven trays. The blend is dried for 18 to 24 hours at 24° C. to 35° C. in a forced-air oven. The dried granules are then sized. Next, magnesium stearate, or another suitable lubricant, is added to the drug granulation, and the granulation is put into milling jars and mixed on a jar mill for 10 minutes. The composition is pressed into a layer, for example, in a Manesty® press or a Korsch LCT press. For a bilayered core, the drug-containing layer is pressed and a similarly prepared wet blend of the push layer composition, if included, is pressed against the drug-containing layer. In the case of formation of the trilayered core, granules or powders of the drug layer composition, barrier layer composition and push layer composition are sequentially placed in an appropriately-sized die with intermediate compression steps being applied to each of the first two layers, followed by a final compression step after the last layer is added to the die to form the trilayered core. The intermediate compression typically takes place under a force of about 50–100 newtons. Final stage compression typically takes place at a force of 3500 newtons or greater, often 3500–5000 newtons. The single, bilayer or trilayer compressed cores are fed to a dry coater press, e.g., Kilian® Dry Coater press, and subsequently coated with the wall materials as described above. One or more exit orifices are drilled in the drug layer end of the dosage form, and optional water soluble overcoats, which may be colored (e.g., Opadry colored coatings) or clear (e.g., Opadry Clear), may be coated on the dosage form to provide the finished dosage form.

In another manufacture the drug and other ingredients comprising the drug layer are blended and pressed into a solid layer. The layer possesses dimensions that correspond to the internal dimensions of the area the layer is to occupy in the dosage form, and it also possesses dimensions corresponding to the second push layer, if included, for forming a contacting arrangement therewith. The drug and other ingredients can also be blended with a solvent and mixed into a solid or semisolid form by conventional methods, such as ballmilling, calendering, stirring or rollmilling, and then pressed into a preselected shape. Next, if included, a layer of osmopolymer composition is placed in contact with the layer of drug in a like manner. The layering of the drug formulation and the osmopolymer layer can be fabricated by conventional two-layer press techniques. An analogous procedure may be followed for the preparation of the trilayered core in which the barrier layer is present. The compressed cores then may be coated with the inner wall material and the semipermeable wall material as described above.

Another manufacturing process that can be used comprises blending the powdered ingredients for each layer in a fluid bed granulator. After the powdered ingredients are dry blended in the granulator, a granulating fluid, for example, poly(vinylpyrrolidone) in water, is sprayed onto the powders. The coated powders are then dried in the granulator. This process granulates all the ingredients present therein while adding the granulating fluid. After the granules are dried, a lubricant, such as stearic acid or magnesium stearate, is mixed into the granulation using a blender e.g., V-blender or tote blender. The granules are then pressed in the manner described above.

The dosage form of the invention is provided with at least one exit orifice. The exit orifice cooperates with the compressed core for the uniform release of drug from the dosage form. The exit orifice can be provided during the manufacture of the dosage form or during drug delivery by the dosage form in a fluid environment of use. The expressions "exit orifice," "delivery orifice" or "drug delivery orifice," and other similar expressions, as used herein include a member selected from the group consisting of a passageway; an aperture; an orifice; and a bore. The expression also includes an orifice that is formed from a substance or polymer that erodes, dissolves or is leached from the outer wall to thereby form an exit orifice. The substance or polymer may include, for example, an erodible poly (glycolic) acid or poly(lactic) acid in the semipermeable wall; a gelatinous filament; a water-removable poly(vinyl alcohol); a leachable compound, such as a fluid removable pore-former selected from the group consisting of inorganic and organic salt, oxide and carbohydrate. An exit, or a plurality of exits, can be formed by leaching a member selected from the group consisting of sorbitol, lactose, fructose, glucose, mannose, galactose, talose, sodium chloride, potassium chloride, sodium citrate and mannitol to provide a uniform-release dimensioned pore-exit orifice. The exit orifice can have any shape, such as round, triangular, square, elliptical and the like for the uniform metered dose release of a drug from the dosage form. The dosage form can be constructed with one or more exits in spaced-apart relation or one or more surfaces of the dosage form. Drilling, including mechanical and laser drilling, through the semipermeable wall can be used to form the exit orifice. Such exits and equipment for forming such exits are disclosed in U.S. Pat. Nos. 3,916,899, by Theeuwes and Higuchi and in U.S. Pat. No. 4,088,864, by Theeuwes, et al., each of which is incorporated in its entirety by reference herein. It is presently preferred, at least on the trilayered dosage form, to utilize two exit orifices of equal diameter.

Reboxetine (free base equivalent) is provided in the drug layer in therapeutically effective amounts for once per day dosing. In accord with the prior art, reboxetine doses of 4–10 mg/day, most commonly 8 mg/day, administered as divided doses in an immediate-release dosage form ingested twice daily, have been found effective for many patients. Following a 4 mg reboxetine (free base equivalent) dose administered as an immediate release tablet, peak plasma reboxetine concentrations of about 130 ng/ml are obtained within 2 hours. *ABPI Compendium of Data Sheets and Summaries of Product Characteristics* 1988–99, Edronax®, product of Pharmacia & Upjohn.

In accord with the above-cited information obtained through experience with the conventional immediate-release dosage form, reboxetine may be provided in the drug layer in the sustained release dosage forms of the present invention in amounts of from less than 1 mg to up to 10 mg or more, if desired. In presently preferred single drug layer embodiments of once-a-day dosage forms in accord with the present invention, the drug layer comprises reboxetine methanesulfonate in a dose of 4 mg reboxetine (free base equivalent) per dosage form. Two different embodiments of such dosage forms are exemplified in Example 1. These different dosage forms had $T_{90}$ values of greater than 12 hours and released reboxetine for a continuous period of time of more than about 22 hours. Within about 2 hours following administration, each of the different dosage forms were releasing reboxetine at a uniform release rate that continued for a prolonged period of time of about 5 hours or more.

In a bilayer embodiment of once-a-day dosage forms in accord with the present invention, the drug layer comprises reboxetine methanesulfonate in a dose of 4 mg reboxetine (free base equivalent) per dosage form. This embodiment is exemplified in Example 2 below. The dosage forms have a $T_{90}$ of about 9 hours or more and provide release of reboxetine for a continuous period of time of at least about 12 hours. Within about 3 hours following administration, reboxetine is being released at a uniform release rate that continues for a prolonged period of time of at least about 7 hours. Following this prolonged period of uniform release rates, drug release continues for several more hours until the dosage form is spent.

In another bilayer embodiment of once-a-day dosage forms in accord with the present invention, the drug layer comprises reboxetine methanesulfonate in a dose of 4 mg reboxetine (free base equivalent) per dosage form. This embodiment is exemplified in Example 3 below. The dosage forms have a $T_{90}$ of about 15 hours or more and release reboxetine for a continuous period of time of at least about 24 hours. Within about 5–6 hours following administration, reboxetine is being released at a uniform release rate that continues for a prolonged period of time of about 7–8 hours or, more preferably, 10 hours or more. Following this prolonged period of uniform release rates, drug release continues for several more hours until the dosage form is spent.

In a trilayer embodiment of once-a-day dosage forms in accord with the present invention, the drug layer comprises reboxetine methanesulfonate in doses of 4, 6, 8 and 10 mg reboxetine (free base equivalent) per dosage form. This embodiment is exemplified in Examples 4–6 below. The dosage forms have a $T_{90}$ of about 15–16 hours or more and release reboxetine for a continuous period of time of at least about 24 hours. Within about 2–6 hours following administration, reboxetine is being released at a uniform release rate that continues for a prolonged period of time of about 7–8 hours or, more preferably, 10 hours or more. Following this prolonged period of uniform release rates, drug release continues for several more hours until the dosage form is spent.

Dosage forms of this invention exhibit sustained release of drug over a continuous time period that includes a prolonged time when drug is released at a uniform release rate as determined in a standard release rate assay such as that described herein. When administered to a subject, the dosage forms of the invention provide blood plasma drug concentrations in the subject that are less variable over a prolonged period of time than those obtained with immediate release dosage forms. When the dosage forms of this invention are administered on a continuous once-a-day basis, the dosage forms of the invention provide therapeutically effective average steady-state plasma reboxetine concentrations while providing steady-state peak plasma reboxetine concentrations that occur at a later time following dose administration and that exhibit a lesser magnitude than the steady-state peak plasma reboxetine concentrations that occur following twice a day administration of an immediate-release reboxetine dosage form.

The invention comprises a method of treating disease states and conditions that are responsive to treatment with reboxetine by orally administering to a subject a sustained release dosage form of reboxetine. The method is practiced with dosage forms that are adapted to release the compound at a uniform release rate of between about 0.2 mg/hr to about 0.6 mg/hr over a prolonged time period of at least about 4 hours, preferably 5–6 hours or more, and most preferably 10 hours or more.

The practice of the foregoing methods by orally administering a reboxetine dosage form to a subject once a day for the treatment of depression is preferred. Other disease states and conditions, which may be manifested or clinically diagnosed as symptoms of depression, may be treated with the reboxetine dosage forms and methods of the invention. In addition, other disease states and conditions which may or may not manifest in association with depression but which may be responsive to treatment with reboxetine may also be treated with the dosage forms and methods of the invention.

Preferred methods of manufacturing dosage forms of the present invention are generally described in the Examples below. All percentages are weight percent unless otherwise noted.

EXAMPLE 1

Osmotic dosage forms comprising a single drug layer in the internal compartment for providing sustained release of reboxetine were made in accord with conventional manufacturing processes known in the art. Two different embodiments, having different weights, i.e., thickness, of the semipermeable membrane, were prepared as follows.

A drug component layer composition was prepared by mixing 3.5 g reboxetine methanesulfonate, 92 g mannitol and 4.0 g hydroxypropylmethylcellulose (Methocel E5 brand name product of Dow Chemical Co., Midland, Mich.) in a beaker with slow addition of 24 ml of ethanol to obtain a consistent granulation. The wet granulation was screened through a 20 mesh screen and dried overnight under ambient conditions. The dried granulation was screened again with a 20 mesh screen. Next, 0.5 g of magnesium stearate was added and mixed for 3 minutes. The granulation was compressed in 150 mg quantities to form single-layer cores containing about 5.25 mg of reboxetine methanesulfonate (about 4.0 mg of reboxetine free base equivalent). Compression was achieved using a Carrer press and standard round concave 9/32" tablet tooling at a force of 0.25 t.

A semipermeable membrane solution was prepared from a mixture containing cellulose acetate (CA 398–10, having an acetyl content of 39.8%, product of Eastman Chemical, Kingsport, Tenn.) and an ethylene oxide-propylene oxide-ethylene oxide triblock copolymer (Poloxamer F68 brand product of BASF Corp., Mt. Olive, N.J.,) in a 75:25 ratio. The two ingredients were dissolved in a blend of 99.5% acetone a nd 0.5% water and the mixture was warmed and mixed for 2.5 hours to form a 5% solids solution. In a pan coater, the solution was then sprayed onto the compressed cores to approximately two different weights: 12.3 mg (dosage form A) and 21.9 mg (dosage form B). One 10 mil drug delivery orifice was drilled into each coated core and the dosage form s were dried in a forced air oven at 45° C. for 16 hours to remove the remaining solvents.

Release rates from three samples of each of the different dosage forms were determined at two-hour intervals for a 22-hour period using in vitro dissolution testing as described elsewhere herein. Both dosage form A and dosage form B exhibited continuous release of reboxetine over this period with $T_{90}$ values of greater than 12 hours and greater than 18 hours, respectively. Release rates from five samples of each of the different dosage forms were also determined hourly for eight hours with the results shown in Table 1.

TABLE 1

| Time (hours) | Average quantity of reboxetine methanesulfonate released from dosage form A | Average quantity of reboxetine methanesulfonate released from dosage form B |
|---|---|---|
| 1 | .309 | .076 |
| 2 | .759 | .390 |
| 3 | .668 | .498 |
| 4 | .620 | .447 |
| 5 | .595 | .390 |
| 6 | .639 | .348 |
| 7 | .371 | .307 |
| 8 | .239 | .281 |

As seen from Table 1, dosage form A began releasing reboxetine at a uniform rate within 2 hours and continued uniform release for about 5 hours, i.e., through the sixth hour. Dosage form B also began releasing reboxetine at a uniform rate within 2 hours and the uniform rate of release continued throughout the measurement period, i.e., through the eighth hour.

EXAMPLE 2

Osmotic dosage forms comprising a bi-layer compressed core consisting of a drug layer and a push layer in the internal compartment for providing sustained release of reboxetine were made in accord with conventional manufacturing processes known in the art. In brief, the drug layer composition, containing reboxetine methanesulfonate, an osmagent and other inactive agents, and the push layer composition, containing osmagents and high viscosity polymers, are separately manufactured using aqueous fluid bed granulation techniques. The compositions are compressed into standard round bi-convex bilayer tablet cores using conventional core compression techniques. Coating of the tablet cores with the semipermeable membrane composition is carried out in a pan coater using acetone/water as the solvent system. The drug delivery orifice is drilled through the membrane on the drug layer side using an automated laser. The dosage forms are then dried to reduce the residual acetone and remove any excess moisture.

Each dosage form as prepared comprised:

| | Drug layer |
|---|---|
| 5.47 mg | reboxetine methanesulfonate (about 4 mg reboxetine free base equivalent using conversion factor of 0.7653 and including adjustments to compensate for a 4% system overage and 99.3% purity of the lot used) |
| 67.08 mg | polyethylene oxide 200K |
| 6.15 mg | sodium Chloride |
| 2.87 mg | povidone K29-32 |
| 0.41 mg | magnesium stearate |
| 0.02 mg | butylated hydroxy toluene |
| | Push layer |
| 43.32 mg | polyethylene oxide 2000K |
| 20.40 mg | sodium chloride |
| 3.40 mg | hydroxypropyl methylcellulose 2910, 5 cps |
| 0.68 mg | red ferric oxide |

-continued

| 0.17 mg | magnesium stearate |
|---|---|
| 0.03 mg | butylated hydroxy toluene |
| | Semipermeable Membrane |
| 15.8 mg | cellulose acetate (39.8% acetyl content) |
| 0.2 mg | polyethylene glycol 3350 |

Preparation of the Drug Layer Granulation

A binder solution is prepared by dissolving povidone K29–32 in water. The sodium chloride is sized through a 40 mesh screen and a fluid bed granulator ("FBG") bowl is charged with the required amounts of reboxetine methanesulfonate, polyethylene oxide 200K (Union Carbide Corporation), sodium chloride and povidone K29–32. The binder solution as prepared above is sprayed into the bowl during mixing. The granulation is dried in the FBG and milled through a 7 mesh screen. Next, the required amounts of antioxidant, butylated hydroxytoluene, and lubricant, magnesium stearate, are sized through a 40 mesh screen and blended into the granulation in a tote or V-blender.

Preparation of the Push Layer Granulation

A binder solution is prepared by dissolving hydroxypropyl methylcellulose 2910 ("HPMC") in water. Sodium chloride powder and red ferric oxide are sized by screening. A fluid bed granulator ("FBG") bowl is charged with the required amounts of polyethylene oxide 2000K, HPMC, sodium chloride and red ferric oxide. After mixing the dry materials in the bowl, the binder solution prepared above is added. The granulation is dried in the FBG until the target moisture content, milled through a 7 mesh screen and transferred to a tote or a blender. The required amounts of butylated hydroxytoluene and magnesium stearate are sized through a 40 mesh screen and blended into the granulation using the tote or V-blender.

Bilayer Core Compression

A bilayer press is set up with standard round 9/32-inch concave punches and dies. Two feed hoppers are placed on the press and the drug layer granulation is placed in one. The drug layer adjustment is performed to produce cores with a uniform target weight. Next, the push layer granulation is placed in the remaining hopper and the second layer adjustment is performed. During compression, the drug layer and push layer bond together producing bilayer cores of uniform core weight, thickness, hardness and friability having lengths of about 4 mm and diameter of about 7 mm.

Preparation of the Semipermeable Membrane and Membrane Coating

Acetone is mixed with the cellulose acetate until the cellulose acetate is completely dissolved. Polyethylene glycol 3350 and water are mixed in separate container. The two solutions are mixed together until the resulting solution is clear. The coating solution has about 5% solids upon application. Bilayer cores prepared as above are placed into a rotating, perforated pan coating unit. The coater is started, and after the desired coating temperature is attained, the coating solution is uniformly applied to the rotating tablet bed until the desired membrane weight gain is obtained.

Drilling and Drying of Membrane Coated Systems

One 25 mil drug delivery orifice is drilled through the coated membrane into the drug layer using an automated laser. The dosage forms are placed in a controlled humidity oven at 45° C. and 45% RH to reduce the residual acetone. Finally, the dosage forms are dried at 45° C. and ambient humidity to remove any excess moisture.

Figure 4:
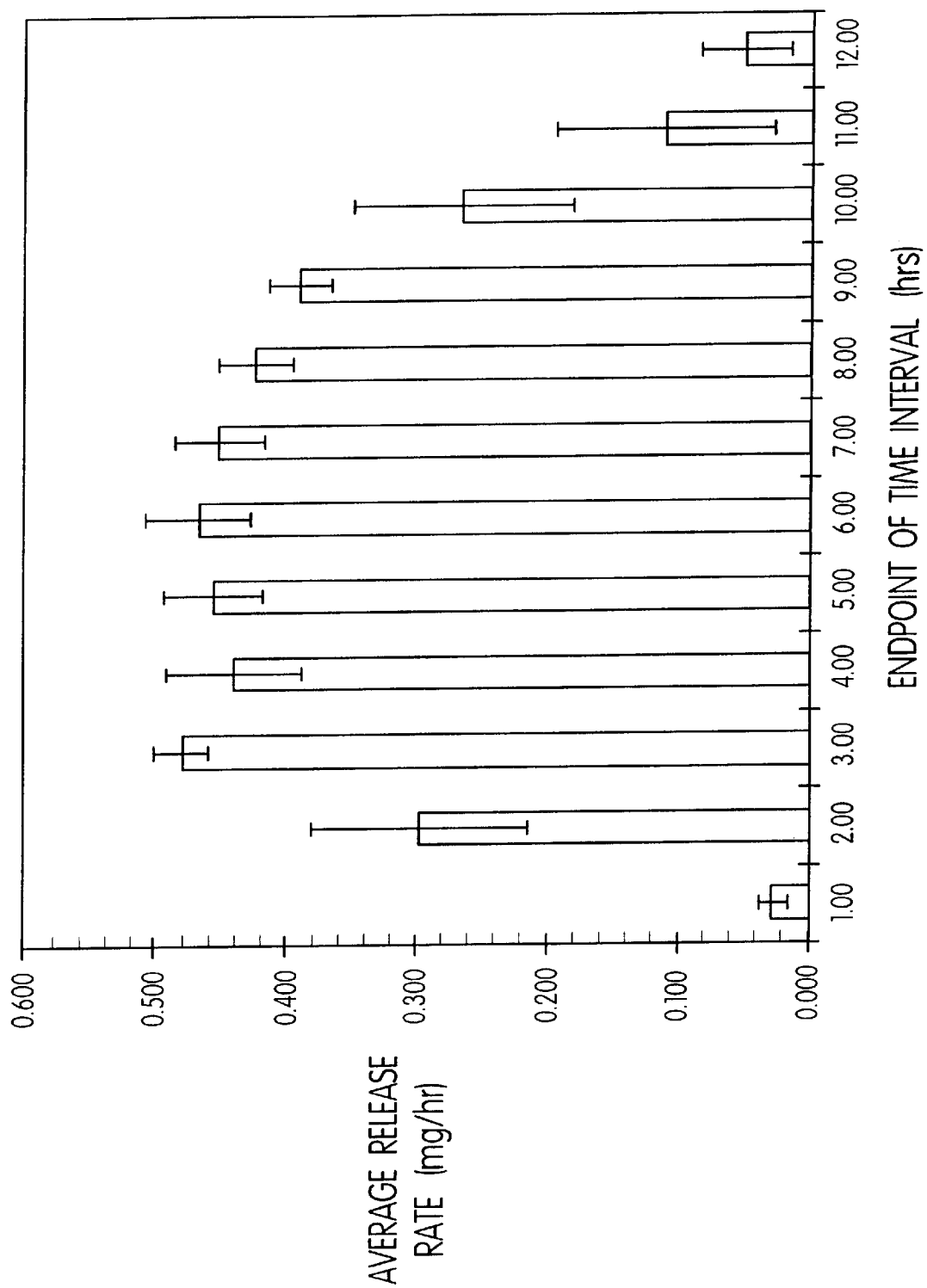
FIG. 4 is a graph illustrating hourly release rates from a dosage form prepared as described in Example 2.

Release rates from twelve samples of the dosage forms prepared as described were determined at hourly intervals for a period of 12 hours using in vitro dissolution testing as described elsewhere herein. The dosage forms exhibited continuous release of reboxetine over this period with a $T_{90}$ value of greater than 9 hours. The average hourly release rates in mg/hr for the 12-hour period were as follows: 0.026; 0.298; 0.483; 0.443; 0.458; 0.470; 0.453; 0.426; 0.393; 0.265; 0.111; and 0.049. These results are shown with standard deviation bars in graph form in FIG. 4. Accordingly, within about 3 hours following administration, reboxetine was being released at a uniform release rate that continued for a prolonged period of time of at least about 7 hours, i.e., through the ninth hour.

EXAMPLE 3

Osmotic dosage forms comprising a bi-layer compressed core consisting of a drug layer and a push layer in the internal compartment for providing sustained release of reboxetine were made in the same manner as described above in Example 2 except the weight of the semipermeable membrane coating was increased. Each dosage form as prepared contained the identical drug layer and push layer components as described above. The semipermeable membrane, however, was increased in weight (and, thus, thickness) to comprise 15.8 mg of cellulose acetate (39.8% acetyl content) and 0.2 mg of polyethylene glycol 3350.

Release rates from twelve samples of the dosage forms prepared as described were determined at two-hourly intervals for a period of 24 hours using in vitro dissolution testing as described elsewhere herein. The dosage forms exhibited continuous release of reboxetine over this period with a $T_{90}$ value of about 18 hours. Average hourly release rates in mg/hr measured at 2 h, 4 h, 6 h, 8 h, 10 h, 12 h, 14 h, 16 h, 18 h, 20 h, 22 h and 24 h were as follows: 0.0013; 0.118; 0.311; 0.255; 0.253; 0.246; 0.237; 0.220; 0.148; 0.068; 0.033; and 0.023. These results are shown with standard deviation bars in graph form in FIG. 5. Accordingly, within about 5–6 hours following administration, reboxetine was being released at a uniform release rate that continued for a prolonged period of time of at least about 11 hours, i.e., through the sixteenth hour.

EXAMPLE 4A–4D

The foregoing general procedures are applied analogously to the preparation of trilayered dosage forms containing 4 mg, 6 mg, 8 mg and 10 mg having the following compositions. The bilayer core compression is modified to include an intermediate compression step to form the barrier layer. An additional coating step is used to form the inner wall. All percentages represent weight percentages. When preparing the maltodextrin-containing drug layer composition, a 10% solution of maltodextrin in water is used as the binder for tableting of the drug layer.

Example 4A

| | Drug layer |
|---|---|
| 5.3 mg (3.7%) | reboxetine methanesulfonate (about 4 mg reboxetine free base equivalent) |
| 135.8 mg (94.3%) | maltodextrin M100 |
| 2.9 mg (2%) | stearic acid (vegetable source) |
| | Push Layer |
| 61.64 mg (63.55%) | polyethylene oxide 7000K |
| 29.1 mg (30%) | sodium chloride |

-continued

| 4.85 mg (5%) | hydroxypropyl methylcellulose 2910, 5 cps |
|---|---|
| 0.39 mg (0.4%) | yellow ferric oxide |
| 0.97 mg (1%) | magnesium stearate |
| 0.05 mg (0.05%) | butylated hydroxy toluene |
| | Barrier Layer |
| 29.7 mg (99%) | ethyl cellulose |
| 0.3 mg (1%) | stearic acid (vegetable source) |
| | Inner Membrane (Subcoat) |
| 17.5 mg (70%) | hydroxypropyl cellulose (Klucel EF) |
| 7.5 MG (30%) | povidone (PVP k29-32) |
| | Applied from 95%/5% ethanol/water. Membrane weight: 25 mg. |
| | Semipermeable Membrane |
| 54.4 mg (99%) | cellulose acetate (39.8% acetyl content) |
| 0.2 mg (1%) | polyethylene glycol 3350 |
| | Membrane weight: 55 mg |

Exit orifice: 30 mil, Tablet dimensions: 5.6 mm diameter and 13.3 mm length

Example 4B

| | Drug layer |
|---|---|
| 7.84 mg (5.5.3%) | reboxetine methanesulfonate (about 6 mg reboxetine free base equivalent) |
| 134.1 mg (92.5%) | maltodextrin M100 |
| 2.9 mg (2%) | stearic acid (vegetable source) |
| | Push Layer |
| 61.64 mg (63.55%) | polyethylene oxide 7000K |
| 29.1 mg (30%) | sodium chloride |
| 4.85 mg (5%) | hydroxypropyl methylcellulose 2910, 5 cps |
| 0.39 mg (0.4%) | yellow ferric oxide |
| 0.97 mg (1%) | magnesium stearate |
| 0.05 mg (0.05%) | butylated hydroxy toluene |
| | Barrier Layer |
| 29.7 mg (99%) | ethyl cellulose |
| 0.3 mg (1%) | stearic acid (vegetable source) |
| | Inner Membrane (Subcoat) |
| 17.5 mg (70%) | hydroxypropyl cellulose (Klucel EF) |
| 7.5 MG (30%) | povidone (PVP k29-32) |
| | Applied from 95%/5% ethanol/water. Membrane weight: 25 mg. |
| | Semipermeable Membrane |
| 54.4 mg (99%) | cellulose acetate (39.8% acetyl content) |
| 0.2 mg (1%) | polyethylene glycol 3350 |
| | Membrane weight: 55 mg |

Exit orifice: 30 mil, Tablet dimensions: 5.6 mm diameter and 13.3 mm length

Example 4C

| | Drug layer |
|---|---|
| 10.45 mg (7.2%) | reboxetine methanesulfonate (about 8 mg reboxetine free base equivalent) |
| 131.7 mg (90.8%) | maltodextrin M100 |
| 2.9 mg (2%) | stearic acid (vegetable source) |
| | Push Layer |
| 61.64 mg (63.55%) | polyethylene oxide 7000K |
| 29.1 mg (30%) | sodium chloride |

-continued

| | |
|---|---|
| 4.85 mg (5%) | hydroxypropyl methylcellulose 2910, 5 cps |
| 0.39 mg (0.4%) | yellow ferric oxide |
| 0.97 mg (1%) | magnesium stearate |
| 0.05 mg (0.05%) | butylated hydroxy toluene |
| | Barrier Layer |
| 29.7 mg (99%) | ethyl cellulose |
| 0.3 mg (1%) | stearic acid (vegetable source) |
| | Inner Membrane (Subcoat) |
| 17.5 mg (70%) | hydroxypropyl cellulose (Klucel EF) |
| 7.5 MG (30%) | povidone (PVP k29-32) |
| | Applied from 95%/5% ethanol/water. |
| | Membrane weight: 25 mg. |
| | Semipermeable Membrane |
| 54.4 mg (99%) | cellulose acetate (39.8% acetyl content) |
| 0.2 mg (1%) | polyethylene glycol 3350 |
| | Membrane weight: 55 mg |

Exit orifice: 30 mil, Tablet dimensions: 5.6 mm diameter and 13.3 mm lenght

Example 4D

| | |
|---|---|
| | Drug layer |
| 13.1 mg (9%) | reboxetine methanesulfonate (about 10 mg reboxetine free base equivalent) |
| 129 mg (89%) | maltodextrin M100, NF |
| 2.9 mg (2%) | stearic acid (vegetable source) |
| | Push Layer |
| 61.64 mg (63.55%) | polyethylene oxide 7000K |
| 29.1 mg (30%) | sodium chloride |
| 4.85 mg (5%) | hydroxypropyl methylcellulose 2910, 5 cps |
| 0.39 mg (0.4%) | yellow ferric oxide |
| 0.97 mg (1%) | magnesium stearate |
| 0.05 mg (0.05%) | butylated hydroxy toluene |
| | Barrier Layer |
| 29.7 mg (99%) | ethyl cellulose |
| 0.3 mg (1%) | stearic acid (vegetable source) |
| | Inner Membrane (Subcoat) |
| 17.5 mg (70%) | hydroxypropyl cellulose (Klucel EF) |
| 7.5 MG (30%) | povidone (PVP k29-32) |
| | Applied from 95%/5% ethanol/water. |
| | Membrane weight: 25 mg. |
| | Semipermeable Membrane |
| 54.4 mg (99%) | cellulose acetate (39.8% acetyl content) |
| 0.2 mg (1%) | polyethylene glycol 3350 |
| | Membrane weight: 55 mg |

Exit orifice: 30 mil, Tablet dimensions: 5.6 mm diameter and 13.3 mm length

EXAMPLE 5

Dosage forms containing the equivalent of 4 mg, 6 mg, 8 mg and 10 mg reboxetine equivalent (as reboxetine methanesulonate) are prepared in accordance with the foregoing procedures and utilizing the foregoing compositions of EXAMPLES 4A–4D, except that the semipermeable wall is prepared with 100% cellulose acetate (CA 398) and two exit orifices, each of 20 mil diameter, are drilled in the drug layer end of the dosage form. The 4 mg, 6 mg, 8 mg and 10 mg dosage forms so prepared exhibit a $T_{90}$ of about 16 hours or more and release reboxetine for a continuous period of time of at least 24 hours.

EXAMPLE 6

Dosage forms are prepared in accordance with the foregoing procedures and utilizing the foregoing compositions of EXAMPLES 4A–4D except that the semipermeable wall is prepared with 88% cellulose acetate (CA 398) and 12% polyvinyl acetate GB 40 (Union Carbide Corporation), and two exit orifices, each of 20 mil diameter, are drilled in the drug layer end of the dosage form. The 4mg, 6 mg, 8 mg and 10 mg dosage forms so prepared exhibit a $T_{90}$ of about 16 hours or more and release reboxetine for a continuous period of time of at least 24 hours.

EXAMPLE 7

A generalized procedure for the preparation of the trilayered dosage form utilizing maltodextrin as the carrier is described below. Percentages of materials will correspond to the dosage forms amounts described above for the particular unit dose of reboxetine. The drug layer consists of maltodextrin, reboxetine and stearic acid. Based on batch size and the particular unit dose of reboxetine in the dosage forms being prepared, suitable quantities of reboxetine and maltodextrin grade M100 (supplied by Grain Processing Incorporated) having a dextrose equivalent (DE) not greater than 20 and reboxetine are agglomerated by spraying a small amount of maltodextrin (1.5 to 1.7 weight %) dissolved in water as a binder solution in a fluid bed granulator. Five weight percent of reboxetine excess may be added to the beginning of the granulation process to compensate for drug loss due to processing. The wet agglomeration or granulation is dried to a target water content end point of 8.5 weight %, with a range of 7.5 to 9.5 weight %. The dried granulation is passed through a 7 mesh screen in a fluid air mill to reduce coarse granules that have formed in the granulation process. The appropriate amount of stearic acid powder then is added to the granulation.

The barrier layer is prepared by blending ethylcellulose powder (Hercules Chemical) and stearic acid powder in a tote bin. The particle size of ethylcellulose is selected based on its capacity to flow and compress during the process of core compression of the three-layer tablet. Generally, ethylcellulose having an overly fine particle size does not flow well during the compression process. A suitable particle size distribution is characterized by 0% being retained on a 20 mesh screen, about 24% being retained on a 40 mesh screen, about 34% being retained on a 60 mesh screen, about 22% being retained on a 100 mesh screen, about 11% being retained on a 200 mesh screen, and about 9% being retained on the pan (less than 300 mesh). While that distribution has been found to be useful, other similar distributions limiting the amount of fines so as not to adversely affect flow during tablet compression may be equivalently usedl for the preparation of the barrier layer.

The push layer is prepared from Polyox 7000K, hydroxypropylethyl cellulose (HPMC), sodium chloride and stearic acid. A small amount of the HPMC is dissolved in water and sprayed as a binder solution to help the powders, Polyox, HPMC and sodium chloride to form an agglomeration using a fluid bed granulation process. The wet granulation is dried to the target endpoint of less than or equal to 0.6 weight % with a range of less than or equal to 2 weight%. The dried granulation is passed through a fluid air mill to minimize large lumps that may have formed in the granulation process, and then the granulation is blended with stearic acid.

The three granulations are charged to a 55 station Korsch rotary press to form trilayer capsule shape tablets using standard tableting techniques on 3/16" deep concave tooling. The order of filling in the die cavity is drug layer, barrier layer and push layer. The drug and barrier layers are tamped with a compression force of about 50–100 newtons and the three layer tablet is compressed under a force of 3500 newtons or greater, typically 3500–5000 newtons at a rate of about 1,100 tablets per minute. Compression at 3500 newtons presently is preferred. The target drug layer weight is 145 mg, with a range of 143 to 147 mg. The target drug layer and barrier layer target weight is 175 mg, with a range of 172 to 178 mg. The total core weight target weight is 272 mg, with a range of 269 to 275 mg. Target core thickness is 13 mm, with a range of 12.8 to 13.2 mm. Target friability is zero percent, with a range of less than or equal to 1%. Typically, friability is on the order of about 0.1%.

The trilayer core is coated on a rotary pan coater, such as the 52" Vector Hi-coater, at a load of either 120 or 240 kg using standard coating techniques to form a 25 mg of subcoat laminate having 70% hydroxypropyl cellulose and 30% PVP K29–32. A coating solution is prepared by dissolving the solids of HPC and PVP in 100% ethanol SDA 3A. A tablet load rotating at 9 RPM is sprayed with the coating solution at a spray rate of 100 ml/min/gun with a range of 90 to 110 ml/min/gun and exhaust temperature of 35° C (range 33° C.–37° C.).

A rate-controlling membrane having a solid formulation of 88% 25 cellulose acetate 398–10 (Eastman Kodak) and 12% polyvinyl acetate GB 40 (Union Carbide) is next coated on top of the subcoat laminate. A membrane coating solution is first prepared by dissolving cellulose acetate 398–10 and polyvinyl acetate in a solvent system of 95/5 weight percent of acetone and water. The rotating tablet load at 9 RPM is sprayed with the coating solution at a rate of 150 ml/min/gun (range 140 to 160) with an exhaust temperature of 35° C. (range 33° C. to 37° C.) to form a membrane laminate of 32 mg (range 30 to 34 mg).

The coated tablets are then dried in a humidity oven at 45° C. and 45% relative humidity for 5 days to remove residual ethanol and acetone. Typically, the combined residual ethanol and acetone concentration in dried tablets is on the order of 1000 parts per million (ppm).

A color overcoat laminate and a clear overcoat laminate may be sequentially applied over the dried tablet for product appearance.

CLINICAL DATA

Plasma concentrations following single doses

The pharmacokinetics of reboxetine dosage forms in accord with the present invention and conventional immediate release dosage forms were compared in a randomized, open-label, single dose, three-way crossover study in 12 healthy male and female subjects. In each treatment, a single 4 mg dose of reboxetine methanesulfonate in an immediate release dosage form and in two different sustained release dosage forms was administered. The two different sustained release dosage forms are described above in Examples 2 and 3 and exhibited $T_{90}$ values of about 9 hours and about 18 hours, respectively.

Figure 5:
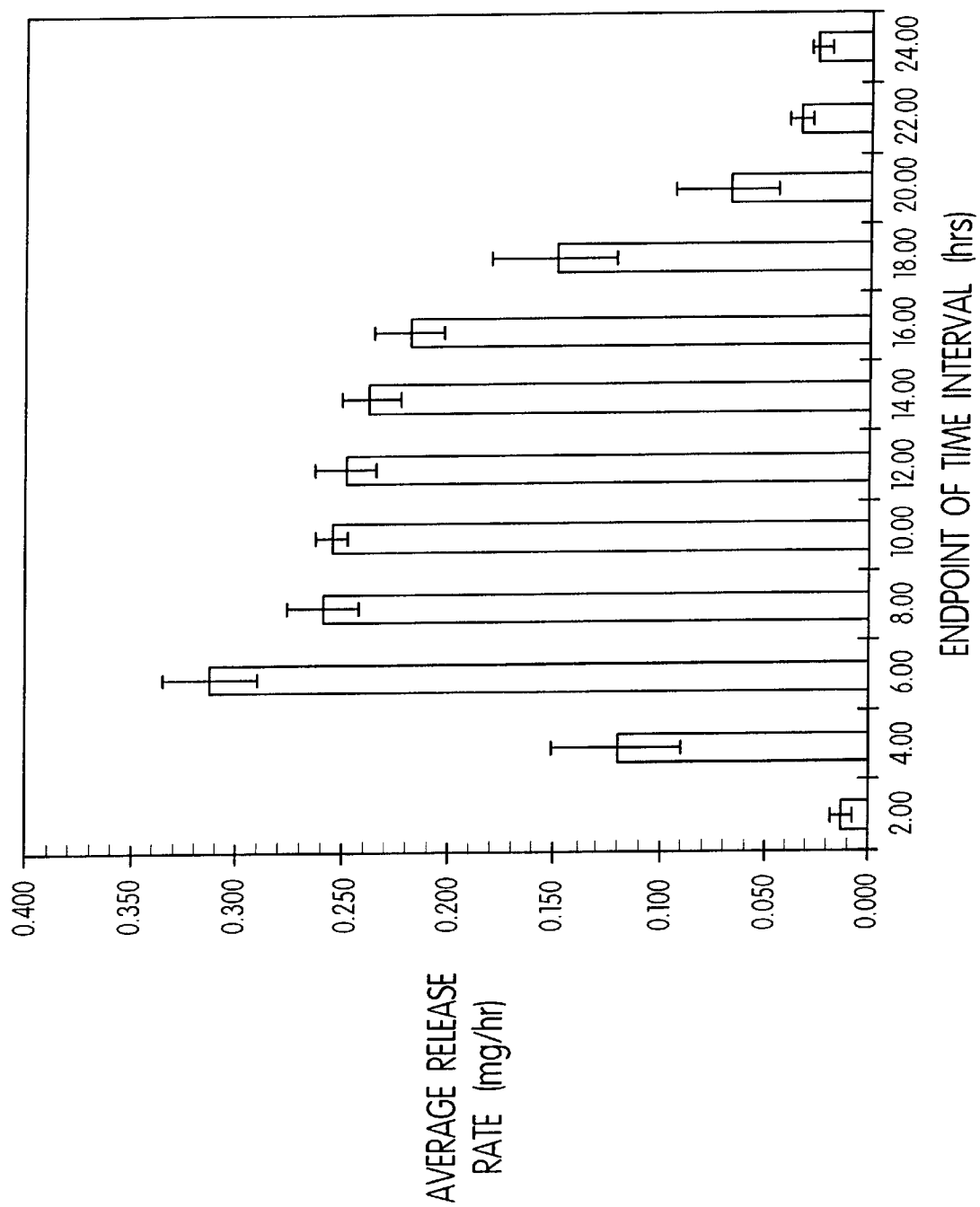
FIG. 5 is a graph illustrating hourly release rates from a dosage form prepared as described in Example 3.

Each single-dose treatment was followed by a seven-day washout period. The resulting plasma reboxetine concentration profiles are shown in FIG. 5 (open circles for the immediate release dosage form, closed circles and stars for the sustained release dosage forms having a $T_{90}$ of about 9 hours and about 18 hours, respectively). The mean $C_{max}$(ng/ml) values were as follows: 117.69 for the immediate release dosage form; 68.38 for the sustained release dosage form having a $T_{90}$ of about 9 hours; and 48.52 for the sustained release dosage form having a $T_{90}$ of about 18 hours. The mean $T_{max}$(h) following administration of the immediate-release dosage form was just 2 hours while following administration of the sustained release dosage forms the mean $T_{max}$ values were 10.7 hours and 23 hours for the sustained release dosage forms having a $T_{90}$ of about 9 hours and about 18 hours, respectively.

Steady-state plasma concentrations

Reboxetine exhibits an elimination half-life ($t_{1/2}$) of about 13 hours. Generally, continuous dosing for a period equal to about four elimination half lives is required to obtain steady-state conditions. Accordingly, steady-state conditions are approached at approximately 52 hours following initiation of a continuous intermittent dosing regimen. Mean steady-state plasma reboxetine concentrations following dosing every 24 hours with 4 mg doses of reboxetine methanesulfonate in two different sustained release dosage forms, having $T_{90}$ values of about 9 hours and about 18 hours, respectively, and following dosing every 12 hours with 2 mg doses of reboxetine methanesulfonate (total daily dose=4 mg) in an immediate release dosage form for a period of four days (96 hours) were simulated.

Figure 6:
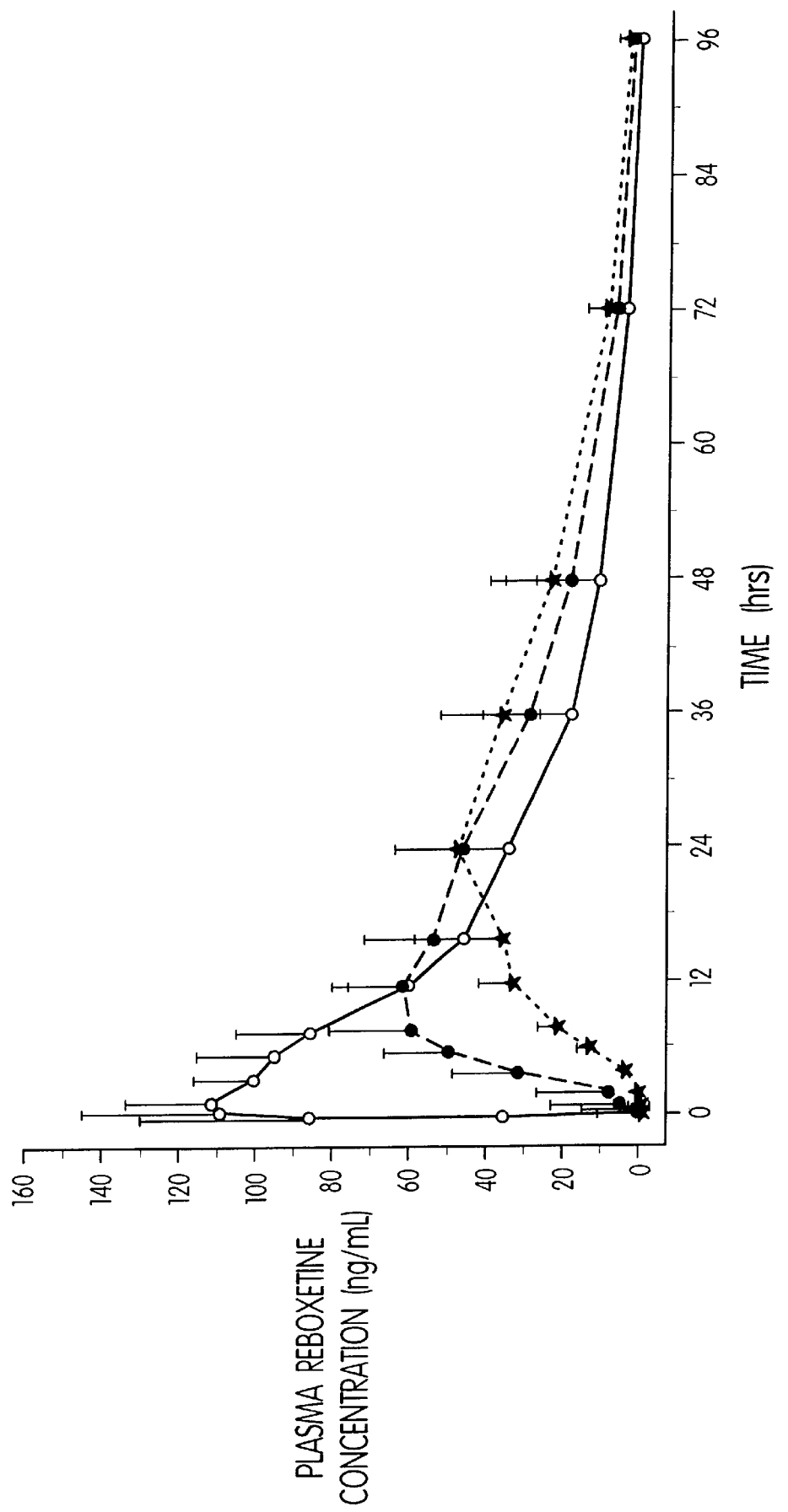
FIG. 6 is a plasma reboxetine concentration profile following single 4 mg doses of three different dosage forms.
Figure 7:
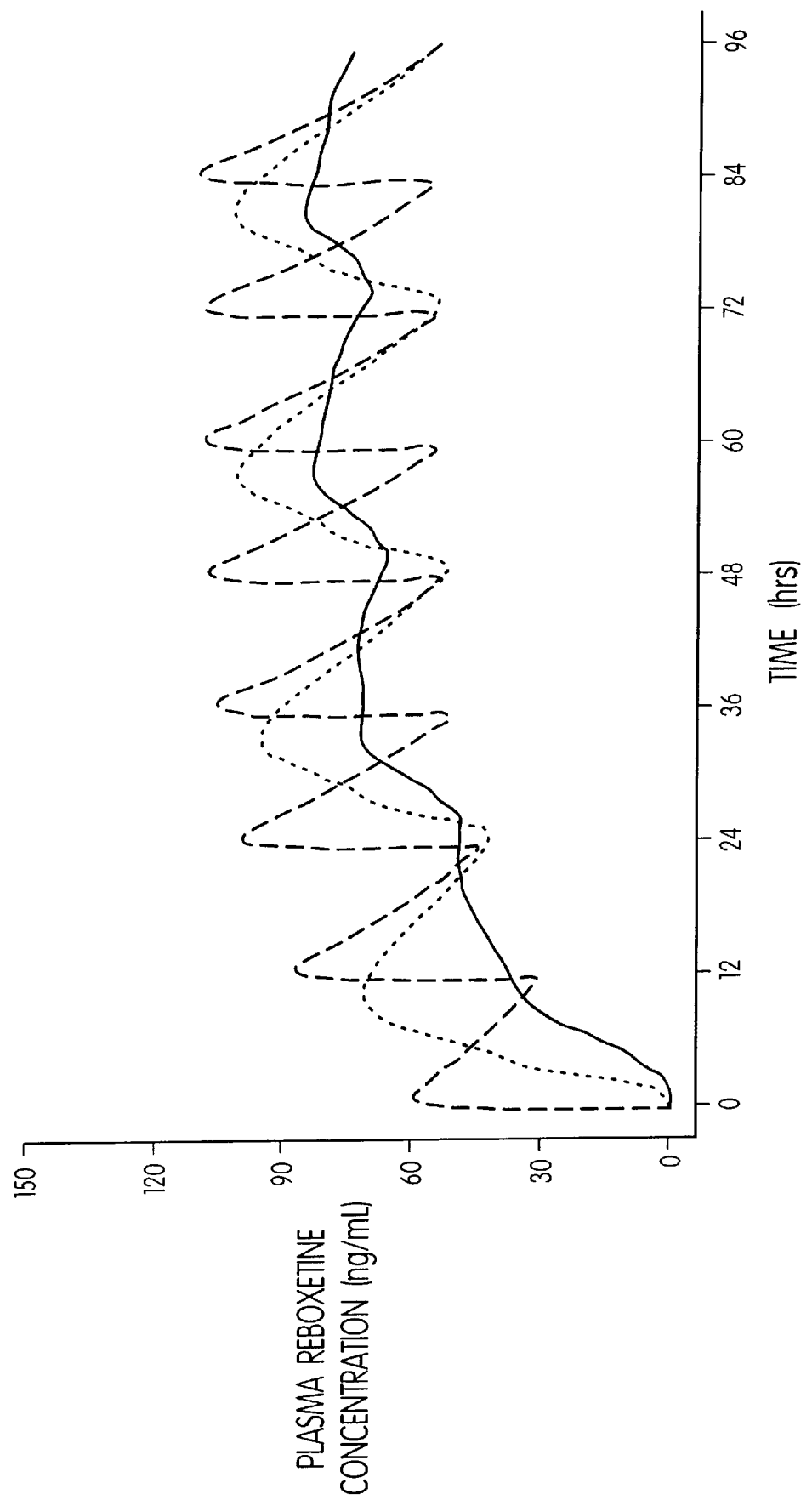
FIG. 7 is a simulated plasma reboxetine concentration profile following continued intermittent dosing with three different dosage forms.

The simulated plasma reboxetine concentration profiles are shown in graph form in FIG. 6 (broken line for the immediate release dosage form and dashed line and solid line for the sustained release dosage forms having a $T_{90}$ of about 9 hours and about 18 hours, respectively). It can be seen that not only are the peak plasma reboxetine concentrations lower following administration of the sustained release dosage forms containing 4 mg of reboxetine than the peak plasma reboxetine concentrations following administration of the immediate release dosage form containing just 2 mg of reboxetine but the number of peak plasma reboxetine concentrations occurring over the four day period with the sustained release dosage form regimens are half the number occurring with the immediate release dosage form regimen, i.e., 4 vs. 8.

Administration of dosage forms in accord with the present invention preferably provides steady-state $C_{max}$/dose ratios of less than about 30 and more preferably less than about 25. The $C_{max}$, $T_{max}$, and $C_{max}$/dose ratios following the doses administered at t=72 hours are shown in Table 2 below:

TABLE 2

| Dose, Dosage Form and Dosing Regimen | $C_{max}$(ng/ml) | $T_{max}$(h) | $C_{max}$/dose ratio |
|---|---|---|---|
| 2 mg immediate release administered every 12 hours | 109.0 | 73.4 | 54.6 |
| 4 mg sustained release ($T_{90}$ = 9 h) administered every 24 hours | 101.9 | 82.0 | 25.4 |
| 4 mg sustained release ($T_{90}$ = 18 h) administered every 24 hours | 85.4 | 81.8 | 21.4 |

In the simulation, the time to steady-state peak plasma reboxetine concentrations are significantly different for the sustained release reboxetine dosage forms compared to the immediate release dosage form. The immediate release dosage form peaks only 1.4 hours following dose administration while the sustained release dosage forms exhibit delayed peaks of 10 hours and 9.8 hours, respectively. The steady-state $C_{max}$/dose ratios following administration of the sustained release dosage forms containing 4 mg of reboxetine are less than half of the ratio following administration of the immediate release dosage form.

The lower magnitude peaks obtained following administration of the sustained release reboxetine dosage forms of the present invention advantageously are less likely to be associated with the occurrence of troublesome side effects in patients. Moreover, the number of peak plasma reboxetine concentrations occurring during each day is halved, and the potential for the occurrence of peak-related side effects is correspondingly reduced by half, with the once a day dosing interval for the sustained release dosage forms of the present invention when compared to the conventional twice a day administration of immediate release reboxetine dosage forms.

In conclusion, while there has been described and pointed out features and advantages of the invention, as applied to present embodiments, those skilled in the art will appreciate that various modifications, changes, additions, and omissions in the descriptions within the specification can be made without departing from the spirit of the invention. In particular, as noted above, there are many approaches to achieving sustained release of drugs from oral dosage forms known in the art. Sustained release reboxetine dosage forms that operate in accord with any approach are encompassed by the scope of the claims below to the extent that the drug release characteristics and/or the plasma reboxetine concentration characteristics as recited in the claims describe those dosage forms either literally or equivalently.

We claim:

1. An osmotic dosage form adapted to release reboxetine at a uniform rate comprising:
    a. a semipermeable membrane defining an internal compartment;
    b. an osmotic composition component comprising reboxetine and a carbohydrate within the internal compartment; and
    c. a delivery orifice formed or formable in the semipermeable membrane through which the reboxetine is delivered.

2. The dosage form of claim 1 wherein the uniform rate is over a prolonged period of time of about four hours or greater.

3. The dosage form of claim 1 wherein the uniform rate is at least about 0.2 mg/hr.

4. The dosage form of claim 1 wherein the release has a $T_{90}$ of at least about 8 hours.

5. The dosage form of claim 1 further comprising: a sweilable polymer component within the internal compartment.

6. The dosage form described in claim 5 wherein the osmotic composition component and the swellable polymer component within the internal compartment are configured as adjacent layers and the delivery orifice is formed or formable through the semipermeable membrane at a location adjacent to the osmotic composition component.

7. The dosage form described in claim 5 further comprising a barrier layer separating the osmotic composition component and the swellable polymer component within the internal compartment and the delivery orifice being formed or formable through the semipermeable membrane at a location adjacent to the osmotic composition component.

8. The dosage form described in claim 7 further comprising an inner wall between the semipermeable membrane and the osmotic composition component, the barrier layer and the swellable polymer component, the delivery orifice being formed or formable through the semipermeable membrane and the inner wall at a location adjacent to the osmotic composition component.

9. A method of treating a condition in a subject responsive to reboxetine, the method comprising orally administering to the subject an osmotic dosage form adapted to release reboxetine at a uniform rate comprising:
    a. a semipermeable membrane defining an Internal compartment;
    b. an osmotic composition component comprising reboxetine and a carbohydrate within the internal compartment; and
    c. a delivery orifice formed or formable in the semipermeable membrane through which the reboxetine is delivered.

10. The method of claim 9 wherein the uniform rate is over a prolonged period of time of about four hours or greater.

11. The method of claim 9 wherein the uniform rate is at least about 0.2 mg/hr.

12. The method of claim 9 wherein the release has a $T_{90}$ of at least about 8 hours.

13. The method of claim 9 wherein the dosage form is administered once a day.

14. The method of claim 13 further comprising producing a therapeutically effective average steady-state plasma reboxetine concentration.

15. The method of claim 9 further comprising producing a steady-state peak plasma reboxetine concentration at a time at least 4 hours following dose administration.

16. The method of claim 9 further comprising producing one peak plasma reboxetine concentration during each 24-hour period.

17. The method of claim 9 further comprising providing steady-state $C_{max}$/dose ratios of less than about 30 and more preferably less than about 25.

18. The dosage form of claim 1 wherein the carbohydrate is selected from the group consisting of maltodextrin, lactose, dextrose, sucrose, mannitol, and sorbitol.

19. The dosage form of claim 18 comprising reboxetine and maltodextrin having a dextrose equivalence (DE) of 20 or less.

20. The dosage of claim 19 wherein the maltodextrin has a dextrose equivalence (DE) of 9–20.

21. The dosage form of claim 1 formed as a tablet compressed under a force of 3500 newtons or greater.

* * * * *